United States Patent
Lizarraga et al.

(10) Patent No.: US 11,052,033 B2
(45) Date of Patent: *Jul. 6, 2021

(54) GUAR HYDROXYPROPYLTRIMETHYLAM-MONIUM CHLORIDE AND USES THEREOF IN HAIR TREATMENT COMPOSITIONS

(75) Inventors: Gilda Lizarraga, Chesterfield, NJ (US); Delphine Mechineau, Massy (FR); Dominique Lemos, Vigneux sur Seine (FR); Caroline Mabille, Paris (FR)

(73) Assignee: RHODIA OPERATIONS, Aubervilliers (FR)

(*) Notice: Subject to any disclaimer, the term of this patent is extended or adjusted under 35 U.S.C. 154(b) by 140 days.

This patent is subject to a terminal disclaimer.

(21) Appl. No.: 14/233,162

(22) PCT Filed: Jul. 20, 2012

(86) PCT No.: PCT/EP2012/064281
§ 371 (c)(1),
(2), (4) Date: Feb. 4, 2014

(87) PCT Pub. No.: WO2013/011122
PCT Pub. Date: Jan. 24, 2013

(65) Prior Publication Data
US 2014/0154200 A1   Jun. 5, 2014

Related U.S. Application Data

(60) Provisional application No. 61/510,304, filed on Jul. 21, 2011.

(51) Int. Cl.
| | | |
|---|---|---|
| A61K 8/73 | (2006.01) |
| A61Q 5/00 | (2006.01) |
| C08B 37/00 | (2006.01) |
| A61Q 5/12 | (2006.01) |
| A61Q 5/02 | (2006.01) |
| C08L 5/00 | (2006.01) |
| A61Q 5/06 | (2006.01) |
| A61Q 19/10 | (2006.01) |

(52) U.S. Cl.
CPC .............. *A61K 8/737* (2013.01); *A61Q 5/00* (2013.01); *A61Q 5/006* (2013.01); *A61Q 5/02* (2013.01); *A61Q 5/12* (2013.01); *C08B 37/0096* (2013.01); *C08L 5/00* (2013.01); *A61Q 5/06* (2013.01); *A61Q 5/065* (2013.01); *A61Q 19/10* (2013.01)

(58) Field of Classification Search
CPC ........................................................ A61K 8/737
See application file for complete search history.

(56) References Cited

U.S. PATENT DOCUMENTS

| | | |
|---|---|---|
| 3,472,840 A | 10/1969 | Stone et al. |
| 4,031,307 A | 6/1977 | Demartino et al. |
| 4,663,159 A | 5/1987 | Brode, II et al. |
| 4,959,464 A | 9/1990 | Yeh |
| 5,387,675 A | 2/1995 | Yeh |
| 5,473,059 A | 12/1995 | Yeh |
| 2001/0051140 A1 | 12/2001 | Wielinga et al. |
| 2010/0029929 A1 | 2/2010 | Luczak et al. |

FOREIGN PATENT DOCUMENTS

| | | |
|---|---|---|
| WO | WO 98/56828 A1 | 12/1998 |
| WO | WO 03/095497 A1 | 11/2003 |
| WO | 2004032887 A1 | 4/2004 |
| WO | WO 2012/042001 A1 | 4/2012 |
| WO | WO 2012/130997 A1 | 10/2012 |

OTHER PUBLICATIONS

Bouillon, Claude, et al, Editors—"The Science of Hair Care", 2nd Edition, 2005, pp. 92-182; 89 pgs.
U.S. Appl. No. 13/984,987, Denis Bendejacq, et al, filed Nov. 27, 2013.

*Primary Examiner* — Bahar Craigo
(74) *Attorney, Agent, or Firm* — Jarrod N. Raphael

(57) ABSTRACT

The present invention relates to a non-cellulosic polysaccharide derivative:
i) having a mean average molecular weight (Mw) from about 100,000 g/mol, preferably from about 150,000 g/mol and more preferably from about 200,000 g/mole to about 2,000,000 g/mol, preferably to about 1,800,000 g/mol and more preferably to about 1,400,000 g/mole; and
ii) containing at least one cationic group, with a cationic degree of substitution ($DS_{cat.}$)$_{extraction}$, from about 0.20 to about 0.30.

16 Claims, 1 Drawing Sheet

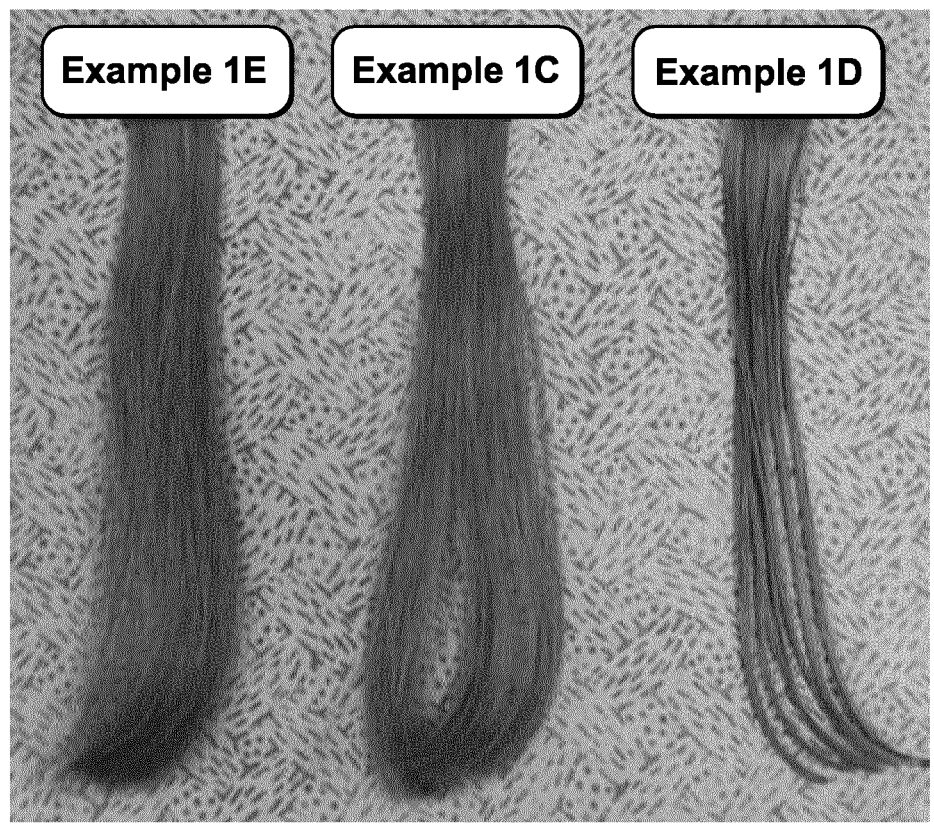

GUAR HYDROXYPROPYLTRIMETHYLAMMONIUM CHLORIDE AND USES THEREOF IN HAIR TREATMENT COMPOSITIONS

CROSS-REFERENCE TO RELATED APPLICATIONS

This application is a U.S. national stage entry under 35 U.S.C. § 371 of International Application No. PCT/EP2012/064281 filed Jul. 20, 2012, which claims priority to U.S. Application No. 61/510,304 filed on Jul. 21, 2011, the whole content of this application being herein incorporated by reference for all purposes.

TECHNICAL FIELD

This invention relates to non-cellulosic polysaccharide derivatives and uses thereof in a hair composition. The invention further relates to hair compositions and a method for providing high conditioning benefits to the hair, by treating hair with a hair composition containing a non-cellulosic polysaccharide derivative.

BACKGROUND ART

Quaternized hydroxyethyl celluloses and cationic guars are widely used in shampoo compositions to provide hair conditioning and deposit ingredients such as silicones or anti-dandruff actives onto hair and/or scalp to further improve the conditioning benefits delivered to hair and provide care to hair and/or scalp. A problem associated with the use of these types of cationic polymers is that it is difficult to obtain a good balance between the conditioning benefits delivered by the polymer alone, its ability to effectively deposit the actives on hair and/or scalp surfaces and the effect of the polymer on hair volume and hair look after drying.

Commercially available quaternized hydroxyethyl celluloses are able to provide high conditioning efficiency by themselves while providing good hair feel and hair appearance after drying. However, they often fail at providing high deposition of ingredients onto the hair and/or scalp surfaces.

On the contrary, commercially available cationic guars provide high deposition efficiency. They are also able to deliver high conditioning benefits by themselves. However, they often fail at providing high conditioning levels while maintaining a pleasant hair feel and hair appearance after drying.

There is still a continuing need for further improvement.

SUMMARY OF THE INVENTION

The aim of the present invention is to provide a new cationic polysaccharide for use in hair composition that is effective in providing:
- conditioning benefits, especially high conditioning benefits, and/or
- high deposition efficiency of ingredients, such as conditioning agents or antidandruff actives, while maintaining a pleasant hair look.

In one embodiment, the present invention is directed to a non-cellulosic polysaccharide derivative:
i) having a mean average molecular weight (Mw) from about 100,000 g/mol to about 2,000,000 g/mol; and
ii) containing at least one cationic group, with a cationic degree of substitution $(DS_{cat})_{extraction}$, from about 0.20 to about 0.30, preferably either from 0.22 to 0.27 or from 0.20 to 0.25 or from 0.25 to 0.30.

It has now been found that by using a selected cationic non-cellulosic polysaccharide derivative, it is possible to combine the benefits described above: high conditioning efficiency and high deposition efficiency while maintaining pleasant dry hair feel attributes.

DETAILED DESCRIPTION OF THE INVENTION

According to the invention, the non-cellulosic polysaccharide derivative may contain one or several cationic groups, said cationic groups being identical or different.

According to the invention, the non-cellulosic polysaccharide derivatives may be selected from galactomannan derivatives, glucomannan derivatives, agar, dextran, polyglucose, polyaminoglycan, xanthan polymers, hemicelluloses (xyloglycans, xyloglucans, mannoglycans and mixed-linkage beta-glucans), pectins (d-galacturonan) and lignin. Preferably, the non-cellulosic polysaccharide derivative is a galactomannan derivative.

Galactomannans are polysaccharides composed principally of galactose and mannose units, wherein the mannose units are linked in a 1-4-β-glycosidic linkage and the galactose branching takes place by means of a 1-6α-linkage to mannose units. Each ring of the galactose or mannose units (or sugar units) bears three free hydroxyl groups that are available for chemical reaction. The galactomannans are usually found in the endosperm of leguminous seeds such as guar, locust bean, honey locust, flame tree, and the like.

In one embodiment, the preferred non-cellulosic polysaccharide starting material used in the present invention is a galactomannan, such as a guar gum, also known as guar. Hence, the non-cellulosic polysaccharide derivative is preferably guar or a guar derivative.

Preferably, the average molecular weight of the non-cellulosic polysaccharide derivative herein is higher than about 150,000 g/mol and more preferably higher than 200,000 g/mol. Preferably, the average molecular weight of the non-cellulosic polysaccharide derivative herein is lower than about 1,800,000 g/mol more preferably lower than 1,400,000 and still more preferably lower than 1,000,000 g/mol.

In particular, the average molecular weight of said polysaccharide is comprised from about 250,000 g/mol to about 800,000 g/mol and more particularly from about 300,000 g/mol to about 600,000 g/mol.

According to a preferred embodiment, the average molecular weight of said polysaccharide is comprised from 200,000 g/mol to about 600,000 g/mol.

As used herein, the "average molecular weight" of the non-cellulosic polysaccharide derivative means the weight average molecular mass of said polysaccharide.

The average molecular weight of the non-cellulosic polysaccharide derivative may be measured by SEC-MALS (Size Exclusion Chromatography with detection by Multi-Angle Light-Scattering detection). A value of 0.140 for do/dc is used for the molecular weight measurements. A Wyatt MALS detector is calibrated using a 22.5 KDa polyethylene glycol standard. All calculations of the molecular weight distributions are performed using Wyatt's ASTRA software. The samples are prepared as 0.05% solutions in the mobile phase (100 mM $Na_2NO_3$, 200 ppm $NaN_3$, 20 ppm pDADMAC) and filtered through 0.45 μm PVDF filters before analysis. The average molecular weights are expressed by weight.

As used herein, the term "cationic groups" refers to positively charged groups and to partially charged groups.

As used herein, the expression "partially charged groups" designates groups which may become positively charged depending of the pH of the formulation. Such groups may also be named "potentially cationic groups".

As used herein, the term "cationic" means at least partially cationic. Thus, the terms "cationizing agents", "cationic groups" and "cationic moieties" include ammoniums (which have a positive charge) but also primary, secondary and tertiary amines and their precursors (which can lead to positively charged compounds).

According to the invention, the non-cellulosic polysaccharide is derivatized or modified so as to contain a cationic group. The resulting compound is the non-cellulosic polysaccharide derivative.

Preferred non-cellulosic polysaccharide derivatives for use in the invention include any galactomannans, such as guars, and galactomannan derivatives, such as hydroxyalkyl guars, for example hydroxyethyl guars or hydroxypropyl guars, that have been modified by chemical means, e.g. quaternization, with one or more derivatizing agents containing reactive groups.

The non-cellulosic polysaccharide derivatives are obtained by reaction between the hydroxyl groups of the galactomannan (and/or the hydroxyl groups of the hydroxyalkyl galactomannan) and the reactive functional groups of the derivatizing agents.

Methods for the preparation of the non-cellulosic polysaccharide derivative are disclosed in U.S. Pat. Nos. 4,663,159; 5,473,059; 5,387,675; 3,472,840; 4,031,307; 4,959,464 and US 2010/0029929, all of which are incorporated herein by reference.

In one embodiment, the non-cellulosic polysaccharide derivatives of the invention result from the reaction of any galactomannans and galactomannan derivatives with a cationizing agent.

Cationizing agents of the present invention are defined as compounds which, by reaction with the hydroxyl groups of the non-cellulosic polysaccharide can lead to a non-cellulosic polysaccharide derivative comprising at least one cationic group according to the invention. Cationizing agents of the present invention are defined as compounds which contain at least one cationic moiety. Cationizing agents comprise agents which can lead to cationic modified non-cellulosic polysaccharide.

A group of suitable derivatizing reagents typically contain a reactive functional group, such as an epoxy group, a halide group, an ester group, an anhydride group or an ethylenically unsaturated group, and at least one cationic moiety or a precursor of such cationic moiety.

As used herein, the term "derivatizing agent" means an agent containing at least a cationic moiety which is grafted to a non-cellulosic polysaccharide. The term "derivatizing agent" encompasses the terms "cationizing agent" and "grafting agent".

In one embodiment of the invention, the cationic moieties may be linked to the reactive functional group of the derivatizing agent by a bivalent linking group, such as an alkylene or oxyalkylene group. Suitable cationic moieties include primary, secondary, or tertiary amino groups or quaternary ammonium, sulfonium, or phosphinium groups.

The derivatizing agent can comprise a cationic moiety, or a precursor of a cationic moiety, that contains a cationic nitrogen moiety, more typically, a quaternary ammonium moiety.

Typical quaternary ammonium moieties are trialkylammonium moieties, such as trimethylammonium moieties, triethylammonium moieties, or tributylammonium moieties, aryldialkylammonium moieties, such as benzyldimethylammonium moieties, and ammonium moieties in which the nitrogen atom is a member of a ring structure, such as pyridinium moieties and imidazoline moieties, each in combination with a counterion, typically a chloride, bromide, or iodide counterion.

According to the invention, examples of cationizing agents, which lead to non-cellulosic polysaccharide derivatives are:

cationic epoxides, such as 2,3-epoxypropyltrimethylammonium chloride, 2,3-epoxypropyltrimethylammonium bromide, 2,3-epoxypropyltrimethylammonium iodide;

chlorohydrin-functional cationic nitrogen compounds, such as 3-halogeno-2-hydroxypropyl trimethylammonium chloride, for example 3-chloro-2-hydroxypropyl trimethylammonium chloride, cationic ethylenically unsaturated monomers or their precursors, such as trimethylammoniumpropyl methacrylamide chloride salt, trimethylammoniumpropyl methacrylamide methylsulfate salt, diallyl dimethyl ammonium chloride, vinyl benzyl trimethylammonium chloride, dimethylaminopropyl methacrylamide (tertiary amine) precursors of cationic monomers, such as N-vinyl formamide, N-vinylacetamide (whose units can be hydrolyzed after polymerization or grafted onto vinyl amine units), Preferably, the cationizing agents, which lead to non-cellulosic polysaccharide derivatives are cationic epoxides, such as 2,3-epoxypropyltrimethylammonium chloride, 2,3-epoxypropyltrimethylammonium bromide and 2,3-epoxypropyltrimethylammonium iodide.

According to the invention, the cationic groups may be introduced into a non-cellulosic polysaccharide by reacting the non-cellulosic polysaccharide starting material with a derivatizing agent which comprises a reactive functional group and at least one cationic moiety (or a precursor of cationic moiety).

According to the invention, the cationic groups present in the non-cellulosic polysaccharide derivative are incorporated into the non-cellulosic polysaccharide starting material by reaction of the hydroxyl groups of said polysaccharide with a cationizing agent.

Preferred cationic groups are chosen from the group consisting of: primary, secondary or tertiary amino groups, quaternary ammonium, sulfonium or phosphinium groups, and mixtures thereof. In a particular preferred embodiment, the cationic groups are trialkylammonium groups, such as trimethylammonium groups, triethylammonium groups, tributylammonium groups, aryldialkylammonium groups, such as benzyldimethylammonium groups, and ammonium groups in which the nitrogen atom is a member of a ring structure, such as pyridinium groups and imidazoline groups, each in combination with a counterion, typically a chloride, bromide, or iodide counterion. Preferably, each cationic group contains at least one cationic charge.

According to an embodiment of the invention, the non-cellulosic polysaccharide derivative may contain other derivatized groups, such as cationic hydrophobic group or hydrophobic group.

Typically, the cationicity of the non-cellulosic polysaccharide derivative can be expressed in terms of degree of substitution.

The cationic degree of substitution may be determined before or after an acidic methanol extraction. The acidic methanol extraction may be considered as a washing step, allowing the removal of the other quaternary ammonium compounds present at the end of the reaction, being it residual cationizing reagent or by-products of unreacted cationizing agent.

In general, the cationic degree of substitution after acidic methanol extraction $(DS_{cat})_{extraction}$ is lower than the cationic degree of substitution before said extraction $(DS_{cat})$.

In the present invention, the cationic degree of substitution determined after the acidic methanol extraction $(DS_{cat})_{extraction}$ is more precise.

As used herein, the $(DS_{cat})$ or $(DS_{cationic})$ relates to the cationic degree of substitution measured before the acidic methanol extraction.

As used herein, the $(DS_{cat})_{extraction}$ or $(DS_{cat})_{extc}$ relates to the cationic degree of substitution measured after the acidic methanol extraction.

As used herein, the expression "cationic degree of substitution" $(DS_{cat})$ or $(DS_{cat})_{extraction}$ means the average number of moles of cationic groups per mole of sugar unit. The $(DS_{cat})$ or $(DS_{cat})_{extraction}$ may be measured by means of $^1$H-NMR (solvent: $D_2O$).

Once the 1H NMR spectrum is obtained, the integration of the multiplet of peaks corresponding to the anomeric proton on all guar units, usually between 3.2-4.3 ppm, is normalized to unity. The peak of interest, the one corresponding to the methyl protons of the quaternary ammonium group on guar units, is centered around 1.8 ppm. This peak is integrated for 9 protons given that there are 3 methyl groups on the ammonium function. Therefore the calculation of the $(DS_{cationic})$ for the case of the cationizing agent 2,3-epoxypropyltrimethylammonium chloride is as follows:

$$DS = \frac{INTEGRAL\_N(Me)3}{INTEGRAL\_anomeric\_proton}/9$$

The measurement of the degree of cationic substitution was made before $(DS_{cationic})$ and after a cleaning protocole $(DS_{cat})_{extraction}$. The true value of degree of cationic substitution is thus considered to be that measured after removal of cationic impurities. Indeed, the presence of the residuals/by-products of the cationic reagent is evidenced by the smaller peaks at lower field than the peak of interest centered around 1.8 ppm and in fact leads to an increase of the apparent value of $(DS_{cationic})$.

According to the present invention, a process of extraction of the non-cellulosic polysaccharide derivative may be carried out in acidified methanol (50:1, MeOH/HCl$_{concentrated\ 37\%}$, v/v) for removing all of cationic reagent impurities. Thus, the non-cellulosic polysaccharide derivative is added to an acidified methanol mixture in a concentration equivalent to approximately 1%, under stirring. This dispersion is then brought to reflux temperatures and held at temperature for 45 minutes. At the end of this process of extraction, the solvent is decanted and the process is repeated twice more with fresh acidified solvent. After the last extraction the resulting non-cellulosic polysaccharide derivative is filtered and washed with pure methanol. The so purified non-cellulosic polysaccharide derivative is then dried and ground before NMR analysis.

According to the present invention, the non-cellulosic polysaccharide derivative has a cationic degree of substitution $(DS_{cat})_{extraction}$, from about 0.20 to about 0.30, for example from about 0.22 to about 0.30, and for example from about 0.25 to about 0.30.

The cationic degree of substitution $(DS_{cat})_{extraction}$ can also be from about 0.20 to about 0.25, or from 0.22 to about 0.27

The cationicity of the non-cellulosic polysaccharide derivative may also be expressed in terms of charge density. The cationic degree of substitution may be converted to a charge density through several methods.

The preferred method for calculating charge density of cationic non-cellulosic polysaccharide derivatives uses a method that specifically quantifies the equivalents of quaternary ammonium groups on said polysaccharide.

For cationic guars obtained by reacting a guar gum with 3-chloro-2-hydroxypropyltrimethylammonium chloride or 2,3-epoxypropyltrimethylammonium chloride, the cationic charge density may be calculated from the cationic degree of substitution using the following equation:

Cationic charge density in mequivalents per gram (meq/g) =

$$\frac{DS_{cat}}{162 + 151 \times DS_{cat}} \times 1000$$

In general, the equation above depends on the group which is grafted to the non-cellulosic polysaccharide.

As used herein, the term "charge density" refers to the ratio of positive charges on a monomeric unit of which a polymer is comprised to the molecular weight of said monomeric unit. The charge density multiplied by the polymer molecular weight determines the number of positively charged sites on a given polymer chain.

According to the present invention, the non-cellulosic polysaccharide derivative has a charge density after the acidic methanol extraction from about 1.0 to about 2 meq/g, for example from about 1.1 to about 1.8 meq/g, and for example from 1.2 to 1.5 meq/g.

The term "non-cellulosic polysaccharide derivative" in the present invention encompasses the terms "cationic non-cellulosic polysaccharide" and "cationically modified non-cellulosic polysaccharide".

As used herein, the expression "cationically modified non-cellulosic polysaccharide" designates non-cellulosic polysaccharide modified by a cationizing agent. Thus, the resulting modified non-cellulosic polysaccharide derivative comprises at least one cationic group.

In the present invention, the preferred non-cellulosic polysaccharide is a guar.

As used herein, the expression "guars" encompasses both guars and hydroxyalkyl guars.

As used herein, the term "hydroxyalkyl guars" relates to guars comprising hydroxyalkyl groups, such as hydroxyethyl or hydroxypropyl groups. In particular, hydroxylalkyl guars are hydroxyethyl guar or hydroxypropyl guar.

In the present invention, the non-cellulosic polysaccharide derivative is preferably a cationic non-cellulosic polysaccharide, such as a cationic guar derivative.

According to the invention, the cationic guar derivative encompasses cationic guar derivative comprising hydroxyalkyl groups or not.

In a preferred embodiment, the present invention is directed to a non-cellulosic polysaccharide derivative, in particular to a guar derivative:
 i) having a mean average molecular weight (Mw) from about 200,000 g/mol to about 600,000 g/mol; and ii) containing at least one cationic group, with a cationic degree of substitution $(DS_{cat})_{extraction}$, from about 0.25 to about 0.30.

In another preferred embodiment, the present invention is directed to a non-cellulosic polysaccharide derivative, in particular to a guar derivative:
i) having a mean average molecular weight (Mw) from about 200,000 g/mol to about 600,000 g/mol; and
ii) containing at least one cationic group, with a cationic degree of substitution $(DS_{cat})_{extraction}$, from about 0.20 to about 0.25.

In another preferred embodiment, the present invention is directed to a non-cellulosic polysaccharide derivative, in particular to a guar derivative:
i) having a mean average molecular weight (Mw) from about 200,000 g/mol to about 600,000 g/mol; and
ii) containing at least one cationic group, with a cationic degree of substitution $(DS_{cat})_{extraction}$, from about 0.22 to about 0.27.

The present invention also relates to the use of the above-mentioned non-cellulosic polysaccharide derivative in a personal care composition. Preferably, the personal care composition is a hair composition.

The present invention also relates to the use of the above-mentioned non-cellulosic polysaccharide derivative in a personal care composition, such as a hair composition, for providing conditioning benefits, especially high conditioning benefits.

In a preferred embodiment, the present invention relates to the use of the non-cellulosic polysaccharide derivative, as defined above, in a hair composition, for:
i) providing conditioning effects to the hair (such as for example improved ease of detangling and/or ease of combing and/or reduced static and/or improved softness); and/or
ii) providing care to hair and/or scalp (such as improved anti-dandruff activity); and/or
iii) providing a nice dry hair appearance (such as an improved hair shine and/or reduced color fading and/or better volume control).

According to the present invention, the non-cellulosic polysaccharide may be used in a hair composition for facilitating hair combing, such as wet hair combing. The wet combability performances may be determined by the measurement of the work required for combing the wet hair. The lower the combing work, the easier the hair to comb.

According to the present invention, the use of the non-cellulosic polysaccharide in a hair composition allows to reduce the wet combing work by at least 25%, for example at least 30%, and for example at least 35%, relative to hair compositions which does not contain any conditioning ingredients.

It is well known that shampooing the hair may result in the hair becoming dry or "frizzy". The hair may also suffer from increased level or static upon drying after shampooing. This can interfere with combing and result in a fly-away hair.

According to the present invention, the non-cellulosic polysaccharide may be used in a hair composition for improving dry hair appearance.

As used herein, the term "dry hair appearance" encompasses the term "dry hair look". The improving of the dry hair appearance may be determined by the manageability of the hair when dry, e.g. less static, less fly-away, and by the aspect of the hair when dry, e.g. softer, shiner, less dry, less frizzy.

It is well known that many shampoo compositions do not provide sufficient deposition of ingredients such as conditioning agents and/or active materials (e.g. antidandruff agents) which are dispersed in the composition during shampooing process. Without such depositions, large proportions of the ingredients are rinsed away during the shampooing process and therefore the shampoos provide little or no conditioning and care benefits to hair and/or scalp.

Dispersed conditioning agents are typically water insoluble, water dispersible, non-volatile, liquids that are in the form of emulsified, liquid particles in the hair composition. They include silicones (e.g., silicone oils, cationic silicones, silicone gums, and silicone resins), mineral oils (e.g. petrolatum), organic oils (e.g., plant oils, animal oils and fatty esters) or combinations thereof.

The dispersed conditioning agent of the compositions of the invention is preferably an insoluble conditioning silicone agent. Non limiting examples of such conditioning silicone agents are described in "The Science of Hair Care", $2^{nd}$ edition, edited by Claude Bouillon and John Wilkinson, 2005. Preferred insoluble conditioning silicone agents include, but are not limited to: dimethicone, amodimethicone and dimethiconol.

The dispersed active materials are typically agents such as UV filters or anti-dandruff agents which are either water insoluble liquids at room temperature or solids. The dispersed active ingredient of the present invention is preferably an anti-dandruff agent. Suitable, non-limiting examples of anti-dandruff particulates include: pyridinethione salts, azoles, selenium sulfide, particulate sulfur, and mixtures thereof.

According to the present invention, the non-cellulosic polysaccharide derivative may be used in a hair composition for improving the deposition efficiency of dispersed conditioning agents and/or active materials.

For instance, when silicone conditioning agents are used, such improvement may be determined by measuring the percentage of silicone deposited onto the hair after the shampooing.

According to the present invention, the use of the non-cellulosic polysaccharide derivative in a hair composition allows to reach deposition percentages, such as conditioning agents deposition percentages and/or active materials deposition percentages, higher than the hair compositions comprising commercially available cationic polysaccharides, such as quaternized hydroxyethyl celluloses.

It has been unexpectedly found that the use of the non-cellulosic polysaccharide derivatives of the invention when incorporated into a functional hair composition is effective for providing high levels of hair detangling, hair combing, deposition of conditioning and/or active ingredients with pleasant hair appearance and hair feel after drying.

It was unexpectedly found that the non-cellulosic polysaccharide derivatives of the invention, when incorporated into hair composition can provide performances equal or greater than similar hair composition containing current commercially available cationic polysaccharides.

Besides, it was also found that the usual build-up commonly seen with typical commercially available cationic polysaccharides upon repeated use of the hair composition, was reduced in the present invention.

In particular, a hair composition comprising the non-cellulosic polysaccharide derivative of the invention provides high wet conditioning benefits such as good wet hair combability, with a reduction in dry hair negatives such as the greasy appearance and coated feel that many consumers experience when conventional cationic polymers with high charge density and high molecular weight are used in shampoo.

The inventors also found that the use of the non-cellulosic polysaccharide in hair shampoo compositions allows providing more stable and richer foam, resulting from the shampoo, than the foam obtained with the same shampoo without the non-cellulosic polysaccharide inside.

It was unexpectedly found that the use of the non-cellulosic polysaccharide derivatives according to the invention is effective in delivering improved conditioning aspects to hair, improved silicone deposition and positive sensory aspects to the hair.

The present invention also relates to a personal care composition comprising at least one non-cellulosic polysaccharide as defined above.

According to the present invention, the personal care composition may contain a mixture of non-cellulosic polysaccharide derivatives.

In one embodiment, the present invention concerns a personal care composition comprising a non-cellulosic polysaccharide derivative which:
   i) has a mean average molecular weight (Mw) from about 100,000 g/mol to about 2,000,000 g/mol; and
   ii) contains at least one cationic group, with a cationic degree of substitution after extraction, $(DS_{cat})_{extraction}$, from about 0.20 to about 0.30.

This non-cellulosic polysaccharide derivative is as defined above.

The personal care compositions include, but are not limited to hair care compositions, skin care compositions such as lotions, creams or sticks, sun care compositions, body cleanser compositions and oral care composition such as toothpastes, oral rinses or anticaries mouth rinses.

According to a preferred embodiment, the personal care composition is a hair composition.

In the present invention, hair compositions include, but are not limited to, hair conditioner, sprays, shampoos, styling gels, serums, masks. Preferably, the hair composition is a shampoo.

In another embodiment, the present invention relates to a hair composition comprising at least one non-cellulosic polysaccharide as defined above.

According to the present invention, the hair composition may contain a mixture of non-cellulosic polysaccharide derivatives.

In a preferred embodiment, the present invention relates to a hair composition comprising a non-cellulosic polysaccharide derivative, preferably a guar derivative, which:
   i) has a mean average molecular weight (Mw) from about 100,000 g/mol to about 2,000,000 g/mol; and
   ii) contains at least one cationic group, with a cationic degree of substitution after extraction, $(DS_{cat})_{extraction}$, from about 0.20 to about 0.30.

According to a preferred embodiment, the present invention relates to a hair composition comprising a non-cellulosic polysaccharide derivative, preferably a guar derivative, which:
   i) having a mean average molecular weight (Mw) from about 100,000 g/mol, preferably form about 150,000 to about 1,800,000, preferably to about 1,400,000 g/mol; and
   ii) containing at least one cationic group, with a cationic degree of substitution after extraction, $(DS_{cat})_{extraction}$, from about 0.20 to about 0.30.

According to another preferred embodiment, the present invention relates to a hair composition comprising a non-cellulosic polysaccharide derivative, preferably a guar derivative, which:
   i) having a mean average molecular weight (Mw) from about 200,000 g/mol to about 600,000 g/mol; and
   ii) containing at least one cationic group, with a cationic degree of substitution after extraction, $(DS_{cat})_{extraction}$, from about 0.25 to about 0.30.

According to another preferred embodiment, the present invention relates to a hair composition comprising a non-cellulosic polysaccharide derivative, preferably a guar derivative, which:
   i) having a mean average molecular weight (Mw) from about 200,000 g/mol to about 600,000 g/mol; and
   ii) containing at least one cationic group, with a cationic degree of substitution after extraction, $(DS_{cat})_{extraction}$, from about 0.20 to about 0.25.

According to another preferred embodiment, the present invention relates to a hair composition comprising a non-cellulosic polysaccharide derivative, preferably a guar derivative, which:
   i) having a mean average molecular weight (Mw) from about 200,000 g/mol to about 600,000 g/mol; and
   ii) containing at least one cationic group, with a cationic degree of substitution after extraction, $(DS_{cat})_{extraction}$, from about 0.22 to about 0.27.

According to an embodiment, the concentration of the non-cellulosic polysaccharide derivative as defined above in the hair composition may be comprised from 0.05% to 5% by weight, for example from 0.075% to 2.5% by weight, for example from 0.1% to 1.0% by weight, and for example from 0.2% to 0.9% by weight, compared to the total weight composition.

It was unexpectedly found that the concentration of the non-cellulosic polysaccharide derivative of the invention in a hair composition may be lower than the concentration of most of the commercially available non-cellulosic cationic polysaccharide, while providing equal or greater conditioning benefits than said commercially polysaccharides.

Such concentrations may vary with the types of hair. Indeed, in the case of damaged hair, higher concentrations of cationic polysaccharide are typically required for better efficiency. However, it is generally observed that the efficiency of the commercially available cationic non-cellulosic polysaccharides cannot be improved while increasing its concentrations without pronounced negatives on dry hair look.

In the present invention, it was unexpectedly found that the increase of the concentration of the non-cellulosic polysaccharide derivative in a hair composition leads to an improved conditioning efficiency without pronounced negatives on dry hair look.

According to an embodiment, the hair composition of the invention may comprise in addition to the non-cellulosic polysaccharide derivative of the invention, other cationic polymers. Non limiting examples of such cationic polymers are described in "The Science of Hair Care", $2^{nd}$ edition, edited by Claude Bouillon and John Wilkinson, 2005.

The hair composition of the invention may also contain further ingredients, such as usual hair composition ingredients. Such ingredients include, but are not limited to: detersive surfactants, nonionic surfactants, zwitterionic surfactants, amphoteric surfactants, cationic surfactants, cationic polymers, dispersed conditioning agents, water soluble silicones (eg. dimethicone copolyols), amphoteric and betainic polymers, nonionic polymers, pearlescent agents, fatty compounds and their derivatives, antidandruff agents, suspending agents, viscosity modifiers, foam boosters, foam stabilizers, protein derivatives, vitamins, amino acids, organic acids, UV absorbers, preservatives, humectants, inorganic salts, inorganic particles, fragrances, dyes, acids, bases, buffers and the like.

The non-cellulosic polysaccharide derivative may be formulated into hair compositions as either leave-on or rinse-off compositions or a combination thereof.

As used herein, the expression "leave-on compositions" designates compositions which are not rinsed with water once applied to the hair.

As used herein, the expression "rinse-off compositions" designates compositions which are rinsed with water once applied to the hair.

The present invention also relates to a method for:
i) providing conditioning effects to the hair in need thereof (such as for example improved ease of detangling and/or ease of combing and/or reduced static and/or improved softness); and/or
ii) providing care to hair in need thereof and/or scalp (such as improved anti-dandruff activity); and/or
iii) providing a nice dry hair appearance (such as an improved hair shine and/or reduced color fading and/or better volume control);
which comprises treating said hair in need thereof with the hair composition as defined above.

In one embodiment, the present invention relates to a method for providing high conditioning efficiency to hair in need thereof, which comprises treating said hair in need thereof with the hair composition as defined above.

The present invention also relates to a method for:
i) providing conditioning effects to the hair in need thereof (such as for example improved ease of detangling and/or ease of combing and/or reduced static and/or improved softness); and/or
ii) providing care to hair in need thereof and/or scalp (such as improved anti-dandruff activity); and/or
iii) providing a nice dry hair appearance (such as an improved hair shine and/or reduced color fading and/or better volume control);
which comprises treating said hair in need thereof with the non-cellulosic polysaccharide as defined above.

In one embodiment, the present invention relates to a method for providing high conditioning efficiency to hair in need thereof, which comprises treating said hair in need thereof with the non-cellulosic polysaccharide as defined above.

In one embodiment, the present invention relates to a method for providing high conditioning efficiency to hair in need thereof, which comprises treating said hair in need thereof with a hair composition, comprising a non-cellulosic polysaccharide derivative:
i) having a mean average molecular weight (Mw) from about 100,000, preferably from about 150,000 g/mol to about 2,000,000 g/mol, preferably to about 1,800,000, more preferably to about 1,400,000; and
ii) containing at least one cationic group, with a cationic degree of substitution after extraction, $(DS_{cat})_{extraction}$, from about 0.20 to about 0.30.

In a preferred embodiment, the present invention relates to a method for providing high conditioning efficiency to hair in need thereof, which comprises treating said hair in need thereof with a hair composition, comprising a non-cellulosic polysaccharide derivative:
i) having a mean average molecular weight (Mw) from about 200,000 g/mol to about 600,000 g/mol; and ii) containing at least one cationic group, with a cationic degree of substitution after extraction, $(DS_{cat})_{extraction}$, from about 0.25 to about 0.30.

In another preferred embodiment, the present invention relates to a method for providing high conditioning efficiency to hair in need thereof, which comprises treating said hair in need thereof with a hair composition, comprising a non-cellulosic polysaccharide derivative:
i) having a mean average molecular weight (Mw) from about 200,000 g/mol to about 600,000 g/mol; and
ii) containing at least one cationic group, with a cationic degree of substitution after extraction, $(DS_{cat})_{extraction}$, from about 0.20 to about 0.25.

In another preferred embodiment, the present invention relates to a method for providing high conditioning efficiency to hair in need thereof, which comprises treating said hair in need thereof with a hair composition, comprising a non-cellulosic polysaccharide derivative:
i) having a mean average molecular weight (Mw) from about 200,000 g/mol to about 600,000 g/mol; and
ii) containing at least one cationic group, with a cationic degree of substitution after extraction, $(DS_{cat})_{extraction}$, from about 0.22 to about 0.27.

According to the invention, the method for providing high conditioning efficiency to hair, consists in contacting the hair with a hair composition, comprising the non-cellulosic polysaccharide derivative, and then, if appropriate, rinsing said hair with water.

According to the invention, the method as defined above allows:
i) providing conditioning effects to the hair in need thereof (such as for example improved ease of detangling and/or ease of combing and/or reduced static and/or improved softness); and/or ii) providing care to hair in need thereof and/or scalp (such as improved anti-dandruff activity); and/or
iii) providing a nice dry hair appearance (such as an improved hair shine and/or reduced color fading and/or better volume control).

According to the invention, the hair in need thereof may be damaged hair, such as mono-bleached, double-bleached and/or permed hair. In a preferred embodiment, the damaged hair used in the present invention is double-bleached or mono-bleached hair.

The expression "mono-bleached hair" used herein means hair which has been discolored once, with an oxidizing agent.

The expression "double-bleached hair" used herein refers to hair which has been discolored with an oxidizing agent, twice.

It was found that the hair composition comprising the non-cellulosic polysaccharide as defined above provides interesting properties to damaged hair.

According to another embodiment, the present invention also relates to a shampoo composition comprising at least one non-cellulosic polysaccharide derivative as defined above.

In one particular embodiment, the present invention relates to a shampoo composition comprising the non-cellulosic polysaccharide derivative as defined above, wherein the non-cellulosic polysaccharide derivative:
i) has a mean average molecular weight (Mw) from about 100,000 g/mol, preferably form about 150,000 to about 2,000,000 g/mol, preferably to about 1,800,000; and
ii) contains at least one cationic group, with a cationic degree of substitution after extraction, $(DS_{cat})_{extraction}$, from about 0.20 to about 0.30.

In a preferred embodiment, the present invention relates to a shampoo composition comprising the non-cellulosic polysaccharide derivative as defined above, wherein the non-cellulosic polysaccharide derivative:
  i) has a mean average molecular weight (Mw) from about 200,000 g/mol to about 600,000 g/mol; and
  ii) contains at least one cationic group, with a cationic degree of substitution after extraction, $(DS_{cat})_{extraction}$, from about 0.25 to about 0.30.

In another preferred embodiment, the present invention relates to a shampoo composition comprising the non-cellulosic polysaccharide derivative as defined above, wherein the non-cellulosic polysaccharide derivative:
  i) has a mean average molecular weight (Mw) from about 200,000 g/mol to about 600,000 g/mol; and
  ii) contains at least one cationic group, with a cationic degree of substitution after extraction, $(DS_{cat})_{extraction}$, from about 0.20 to about 0.25.

In another preferred embodiment, the present invention relates to a shampoo composition comprising the non-cellulosic polysaccharide derivative as defined above, wherein the non-cellulosic polysaccharide derivative:
  i) has a mean average molecular weight (Mw) from about 200,000 g/mol to about 600,000 g/mol; and
  ii) contains at least one cationic group, with a cationic degree of substitution after extraction, $(DS_{cat})_{extraction}$, from about 0.22 to about 0.27.

According to the present invention, the shampoo may comprise silicone as defined previously.

FIG. 1 highlights the hair appearance after one single application for shampoos containing 0.8% of polymer.

The following examples will serve to illustrate the invention, all parts and percentages being by weight, unless otherwise indicated.

EXAMPLE

Suppliers

Jaguar® C500, Jaguar® C17, Jaguar® C13 s, Jaguar® C14 s: Rhodia Novecare
Ucare® JR400, Ucare® JR30M: Amerchol
2,3-epoxypropyltrimethylammonium chloride: Sachem A. Wet Combing and Dry Hair Look Performance Assessment To assess the wet combing and dry hair look properties of the shampoos, flat calibrated tresses of bleached Caucasian hair weighing about 1.5 grams were used. They were purchased from IHIP, International Hair Importers & Products, 87-29 Myrtle Avenue Glendale, N.Y. 11385, USA.

Prior to being actually shampooed, the hair tresses were first cleansed with a 10% active sodium laureth sulfate (SLES) solution. For this cleansing step, the hair tresses were wetted with 37° C. running water for 60 seconds, washed for 60 seconds with 3.0 ml of the SLES solution and then they were rinsed under 37° C. running water for 60 seconds. In a second step, each hair tress was rewetted under running water for 60 seconds and shampooed by applying 0.2 gram of shampoo per gram of hair along the hair length. The tress was kneaded for 45 seconds and then it was rinsed under 37° C. running water for 30 seconds. The shampooed hair tresses were then gently hand combed to remove major tangles and then combed for ten times at 300 mm/min using a MTT 170 Miniature Tensile Tester (Dia-Stron Ltd) equipped with an ACE hard rubber fine tooth comb. Between each combing cycle, the hair was rewetted with water to keep it wet. Combing force versus displacement curves were obtained in the process. Total combing works (corresponding to the integral of this signal) are extracted. From the 10 combing cycle data, the average wet combing work was calculated for each hair tress. For each formulation, a minimum of three hair tresses were assigned and used to determine the average total combing work for the formulation. The lower the total work, the higher the wet conditioning efficiency of the formulation. The tresses were then hung vertically and stored overnight in a climatic room at about 21° C.±5° C. and about 50% relative humidity. The next day, dry hair look was visually assessed and a picture of the hair tresses was taken using a video camera B. Silicone Deposition Measurement The deposition efficiency of shampoos was measured on calibrated Virgin Medium Brown Caucasian Hair (hair tress weight: 4.5 grams; length below epoxy blue clip: 20 cm) purchased from IHIP (International Hair Importers & Products Inc.).

The method contains 4 steps: the pre-treatment of the hair tresses with a 10% SLES (sodium lauryl ether sulfate) solution, the treatment of the hair tresses with the shampoo, the dimethicone extraction using THF (Tetrahydrofuran) and the dosage of the extracted dimethicone using GPC.

Hair Tress Pre Treatment:

Hair tresses were pre-treated with a 10% SLES solution, then rinsed with water prior to treatment with the dimethicone-containing shampoo. The procedure was as follows: each tress was put under a controlled water flow (150 mL/min at 38° C.) for 1 minute, then 3 mL of a 10 wt % SLES solution was applied along the hair tress. Finally, the hair tress was rinsed under running water for 1 minute.

Hair Treatment:

Approximately 450 mg of shampoo were weighed out precisely. The hair tress was rolled around the finger and the shampoo was withdrawn with it. Then, the product was massaged into the hair for 45 s, and precaution was taken to be sure that the product was distributed evenly across the tress assembly. The hair tress was then rinsed under running water for 30 s. The excess water was stripped off from the tress by pulling through middle finger and forefinger and the hair tress was left to dry and equilibrate overnight in a climatic room (21° C., 50% H.R.)

Silicone Extraction:

For each hair tress, 250 ml polyethylene bottles were tarred. The hair tress was introduced in the bottle while maintaining the mounting tab outside the bottle. The hair was cut just below the mounting tab and the amount of hair introduced in the bottle was recorded. Then, about 100 ml of THF were introduced in each of the polyethylene bottles, before capping them. All the bottles were placed on the agitation table and left to mix for 24 hours at 200 rpm. Under the hood, the THF extraction solution was transferred in a 150 ml evaporating dish and left to evaporate (maximum ventilation rate) for 24 hours under the hood.

Dosage of the Extracted Dimethicone:

The evaporating dish capped was tarred with a watch glass. Under the hood, about 4 ml of THF were introduced in the evaporating dish. Using a spatula, the dimethicone deposited onto the walls of the evaporating dish was re-dissolved. Once the silicone was re-solubilized, the evaporating dish capped was weighed with the watch glass and the amount of THF introduced was recorded. Using a syringe, the dimethicone solution was transferred in a 2 ml vial and the vial was capped. The dimethicone concentration was dosed in the vial using GPC. The amount of dimethicone deposited on hair, Q, expressed in ppm (µg of dimethicone per g of hair) was calculated as follows:

$$Q \text{ (μg dimethicone per gram of hair)} = \frac{C_{dimethicone} \times m_{THF}}{m_{hair}}$$

where $C_{dimethicone}$ is the dimethicone concentration in the GPC vial expressed in ppm (μg dimethicone per gram of THF), $m_{THF}$ the amount of THF, expressed in grams, used to re-solubilize the dimethicone in the evaporating dish and $m_{hair}$ the amount of hair expressed in grams introduced in the polyethylene bottle. The deposition yield was calculated as follows:

$$R\ (\%) = \frac{C_{dimethicone} \times m_{THF}}{m_{shampoo} \times \phi}$$

where $m_{shampoo}$ is the amount of shampoo, expressed in micro-grams, used to treat the hair tress and φ, the concentration of dimethicone in the shampoo. A minimum of 2 hair tresses were used for each formulation to calculate an average amount of silicone deposited on hair and an average deposition yield.

C. Synthesis of the Non Cellulosic Polysaccharide Derivatives

1) Synthesis of Polymer 1

The polymer of the present invention was made in the following manner:

In a 1 liter stirred reactor, 183 g of isopropanol solvent mixed with 85 g of de-ionized water were introduced at room temperature, under a blanket of inert nitrogen gas. 103 g of guar flour, (molecular weight of 1-2 million g/mol and a particle size of 200-500 micron) were then loaded at room temperature and under vigorous stirring. After a few minutes of stirring to allow for homogenization the pH of the dispersion was adjusted with the addition of 5 g of acetic acid, 99%. 5 g of peracetic acid, 32% solution in dilute acetic acid, were added to effect the depolymerization of guar. Once homogenization is allowed by mixing for 30 minutes, the dispersion was heated to 50° C. and held at this temperature until most peracetic acid was consumed, as measured using peroxide strips (<24 hours).

Once the depolymerization was finished the reaction temperature was lowered to room temperature and 66 g of 2,3-epoxypropyltrimethylammonium chloride were added, followed by 40 g of isopropanol solvent. This reagent was left to mix at room temperature with the guar dispersion for 20 minutes, after which 25.5 g of sodium hydroxide (25%), were added slowly. The dispersion was then heated to 65° C. and held at this temperature for 90 minutes, after which the temperature was lowered to at least 50° C. in order to start the washing procedure.

A reaction mixture obtained as described in the paragraph above was dispersed under stirring with 178 g of isopropanol and 39 g of water. It was then left under stirring for 15 minutes and then discharged from the reactor. This dispersion was then filtered under vacuum through qualitative filter paper. This washing and filtering procedure was repeated twice more for 30 minute intervals with 240 g of isopropanol mixed with 39 g of water. The obtained guar powder was finally mixed with 300 g of isopropanol, left to stir for 30 minutes, and filtered. The collected solids were then left to dry overnight in air and then for 4 h in a vacuum oven at 50° C.

The cationic degree of substitution $(DS_{cationic})_{extraction}$ was measured according to the procedure detailed in the description.

The analytical results obtained for the above sample yielded a $DS_{cationic}$ by 1H NMR before acidic extraction of 0.33 and a $(DS_{cationic})_{extraction}$ of 0.25 by 1H NMR after acidic extraction.

The average molecular weight of the non-cellulosic polysaccharide derivative was measured by SEC-MALS analyses according to the procedure detailed in the description and using the following conditions:

Column: Shodex OHpak SB-806M HQ, 3 columns
Mobile phase: 100 mM $Na_2NO_3$, 200 ppm $NaN_3$, 20 ppm pDADMAC
Flow rate: 1.0 ml/min
Detector: Agilent Refractive Index Detector, Wyatt mini DAWN TRISTAR MALS detector
Injection volume: 100 μl
Temperature: ambient
Run time: 50 minutes The molecular weight was $3.33 \times 10^5$ g/mol.

2) Synthesis of Polymer 2

The polymer of the present invention was made in the following manner:

In a 1 liter stirred reactor, 183 g of isopropanol solvent mixed with 85 g of de-ionized water were introduced at room temperature, under a blanket of inert nitrogen gas. 103 g of guar flour, (molecular weight of 2-3 million g/mol and a particle size of 200-500 micron) were then loaded at room temperature and under vigorous stirring. After a few minutes of stirring to allow for homogenization 4 g of peracetic acid, 32% solution in dilute acetic acid, were added to effect the depolymerization of guar. Once homogenization is allowed by mixing for 30 minutes, the dispersion was heated to 50° C. and held at this temperature until most peracetic acid was consumed, as measured using peracetic acid strips (<24 hours).

Once the depolymerization was finished the reaction temperature was lowered to room temperature and 55 g of 2,3-epoxypropyltrimethylammonium chloride were added, followed by 80 g of isopropanol solvent. This reagent was left to mix at room temperature with the guar dispersion for 20 minutes, after which 20 g of sodium hydroxide (25%), were added slowly. The dispersion was then heated to 65° C. and held at this temperature for 90 minutes, after which the temperature was lowered to at least 50° C. in order to start the washing procedure.

A reaction mixture obtained as described in the paragraph above was dispersed under stirring with 178 g of isopropanol, 39 g of water and 4 g of acetic acid. It was then left under stirring for 15 minutes and then discharged from the reactor. This dispersion was then filtered under vacuum through qualitative filter paper. This washing and filtering procedure was repeated twice more for 30 minute intervals with 240 g of isopropanol mixed with 39 g of water. The obtained guar powder was finally mixed with 300 g of isopropanol, left to stir for 30 minutes, and filtered. The collected solids were then left to dry overnight in air and then for 4 h in a vacuum oven at 50° C.

The cationic degree of substitution $(DS_{cationic})_{extraction}$ was measured according to the procedure detailed in the description.

The analytical results obtained for the above sample yielded a $DS_{cationic}$ by 1H NMR before acidic extraction of 0.30 and a $(DS_{cationic})_{extraction}$ of 0.28 by 1H NMR after acidic extraction.

The average molecular weight of the non-cellulosic polysaccharide derivative was measured by SEC-MALS analyses according to the procedure detailed in the description and using the following conditions:

Column: Shodex OHpak SB-806M HQ, 3 columns
Mobile phase:100 mM $Na_2NO_3$, 200 ppm $NaN_3$, 20 ppm pDADMAC
Flow rate: 1.0 ml/min
Detector: Agilent Refractive Index Detector, Wyatt mini DAWN TRISTAR MALS detector
Injection volume: 100 μl
Temperature: ambient
Run time: 50 minutes The molecular weight was $1.19 \times 10^6$ g/mol 3) Synthesis of Polymer 3

The polymer of the present invention was made in the following manner:

In a 1 liter stirred reactor, 183 g of isopropanol solvent mixed with 85 g of de-ionized water were introduced at room temperature, under a blanket of inert nitrogen gas. 103 g of guar flour, (molecular weight of 2-3 million g/mol and a particle size of 200-500 micron) were then loaded at room temperature and under vigorous stirring. After a few minutes of stirring to allow for homogenization 11 g of peracetic acid, 32% solution in dilute acetic acid, were added to effect the depolymerization of guar. Once homogenization is allowed by mixing for 30 minutes, the dispersion was heated to 50° C. and held at this temperature until most peracetic acid was consumed, as measured using peracetic acid strips (<24 hours).

Once the depolymerization was finished the reaction temperature was lowered to room temperature and 68 g of 2,3-epoxypropyltrimethylammonium chloride were added, followed by 80 g of isopropanol solvent plus 20 g of water. This reagent was left to mix at room temperature with the guar dispersion for 20 minutes, after which 27 g of sodium hydroxide (25%), were added slowly. The dispersion was then heated to 65° C. and held at this temperature for 90 minutes, after which the temperature was lowered to at least 50° C. in order to start the washing procedure.

A reaction mixture obtained as described in the paragraph above was dispersed under stirring with 178 g of isopropanol, 39 g of water and 2 g of acetic acid. It was then left under stirring for 15 minutes and then discharged from the reactor. This dispersion was then filtered under vacuum through qualitative filter paper. This washing and filtering procedure was repeated twice more for 30 minute intervals with 240 g of isopropanol mixed with 39 g of water. The obtained guar powder was finally mixed with 300 g of isopropanol, left to stir for 30 minutes, and filtered. The collected solids were then left to dry overnight in air and then for 4 h in a vacuum oven at 50° C.

The cationic degree of substitution $(DS_{cationic})_{extraction}$ was measured according to the procedure detailed in the description.

The analytical results obtained for the above sample yielded a $DS_{cationic}$ by 1H NMR before acidic extraction of 0.36 and a $(DS_{cationic})_{extraction}$ of 0.23 by 1H NMR after acidic extraction.

The average molecular weight of the non-cellulosic polysaccharide derivative was measured by SEC-MALS analyses according to the procedure detailed in the description and using the following conditions:
Column: Shodex OHpak SB-806M HQ, 3 columns
Mobile phase:100 mM $Na_2NO_3$, 200 ppm $NaN_3$, 20 ppm pDADMAC
Flow rate: 1.0 ml/min
Detector: Agilent Refractive Index Detector, Wyatt mini DAWN TRISTAR MALS detector
Injection volume: 100 μl
Temperature: ambient
Run time: 50 minutes The molecular weight was $3.05 \times 10^5$ g/mol.

4) Synthesis of Polymer 4

The polymer of the present invention was made in the following manner:

In a 1 liter stirred reactor, 183 g of isopropanol solvent mixed with 73 g of de-ionized water were introduced at room temperature, under a blanket of inert nitrogen gas. 103 g of guar flour, (molecular weight of 2-3 million g/mol and a particle size of 200-500 micron) were then loaded at room temperature and under vigorous stirring. After a few minutes of stirring to allow for homogenization, 14 g of hydrogen peroxide, 4% solution, were added slowly to effect the depolymerization of guar, followed by the addition of 45 g of sodium hydroxide (25%).

Once homogenization is allowed by mixing for 15 minutes, the dispersion was heated to 45° C. and held at this temperature until most peroxide was consumed, as measured using peroxide strips (<5 hours).

Once the depolymerization was finished the reaction temperature was lowered to room temperature and 96 g of isopropanol solvent were added, followed by 77 g of 2,3-epoxypropyltrimethylammonium chloride. This reagent was left to mix at room temperature with the guar dispersion for 20 minutes. The dispersion was then heated to 65° C. and held at this temperature for 90 minutes, after which the temperature was lowered to at least 50° C. in order to start the washing procedure.

A reaction mixture obtained as described in the paragraph above was dispersed under stirring with 178 g of isopropanol, 39 g of water and 12 g of acetic acid. It was then left under stirring for 15 minutes and then discharged from the reactor. This dispersion was then filtered under vacuum through qualitative filter paper. This washing and filtering procedure was repeated twice more for 30 minute intervals with 240 g of isopropanol mixed with 39 g of water. The obtained guar powder was finally mixed with 300 g of isopropanol, left to stir for 30 minutes, and filtered. The collected solids were then left to dry overnight in air and then for 4 h in a vacuum oven at 50° C.

The cationic degree of substitution $(DS_{cationic})_{extraction}$ was measured according to the procedure detailed in the description.

The analytical results obtained for the above sample yielded a $DS_{cationic}$ by 1H NMR before acidic extraction of 0.38 and a $(DS_{cationic})_{extraction}$ of 0.28 by 1H NMR after acidic extraction.

The average molecular weight of the non-cellulosic polysaccharide derivative was measured by SEC-MALS analyses according to the procedure detailed in the description and using the following conditions:
Column: Shodex OHpak SB-806M HQ, 3 columns
Mobile phase:100 mM $Na_2NO_3$, 200 ppm $NaN_3$, 20 ppm pDADMAC
Flow rate: 1.0 ml/min
Detector: Agilent Refractive Index Detector, Wyatt mini DAWN TRISTAR MALS detector
Injection volume: 100 μl
Temperature: ambient
Run time: 50 minutes The molecular weight was $3.68 \times 10^5$ g/mol.

D. Wet Combing and Dry Hair Look Performances of the Polymers

The polymers of the invention as prepared above were formulated into the shampoo composition described below to evaluate their wet combing performances and for some of them, their dry hair look attributes. All ingredients are expressed by weight percent of the total formulation and as level of active ingredient. The results of the wet combing evaluation are reported in Table 1 and the ones on dry hair look in FIG. 1. The performances of the four polymers were assessed through 4 sets of measurements.

| Ingredients | Parts by weight active % |
|---|---|
| Sodium Laureth Sulfate | 14 |
| Disodium Cocoamphodiacetate | 2 |
| Cationic Polymer | 0.5 to 0.8 |
| Sodium Chloride | 1.35 |
| Citric acid to pH 6.0-6.5 | qs |
| Preservative | qs |
| Water | to 100 |

The fourth set of measurements shows that the improvements brought by the polymers of the invention at a dosage of 0.8% are maintained when the polymer dosage is reduced down to 0.5%: polymer 1 and polymer 4 are able to deliver significant improvement of the wet combing performance versus Jaguar® C14 s E. Silicone Deposition Performances of the Polymers The polymers of the invention as prepared above were formulated into the shampoo composition described below to evaluate their silicone deposition efficiency. All ingredients are expressed by weight percent of the total formulation and as level of active ingredient. The results of the silicone deposition measurements are reported in Table 2. The performances of the four polymers were assessed through 4 sets of measurements.

TABLE 1

| Set | Example | Cationic polymer | Mw (g/mol) | DS cat | Charge density (meq/g) | Polymer level in the shampoo (%) | Total wet combing work (J) | Mean error (J) |
|---|---|---|---|---|---|---|---|---|
| Set 1 | Ex 1A (comparative) | none | — | — | — | 0 | 0.45 | 0.07 |
| | Ex 1B (comparative) | Jaguar ® C500 | 389 000 | 0.13 [b] | 0.72 | 0.8 | 0.32 | 0.03 |
| | Ex 1C | Polymer 1 | 333 000 | 0.25 [b] | 1.25 | 0.8 | 0.11 | 0.00 |
| | Ex 1D (comparative) | Jaguar ® C17 | 2 000 000 | 0.20 [b] | 1.04 | 0.8 | 0.10 | 0.01 |
| | Ex 1E (comparative) | Ucare ® JR400 | 450 000 | — | 1.3 [a] | 0.8 | 0.10 | 0.01 |
| Set 2 | Ex 1F | Polymer 1 | 333 000 | 0.25 [b] | 1.25 | 0.8 | 0.16 | 0.05 |
| | Ex 1G | Polymer 3 | 305 000 | 0.23 [b] | 1.17 | 0.8 | 0.13 | 0.01 |
| | Ex 1H (comparative) | Jaguar ® C14s | 2 000 000 | 0.13 [b] | 0.72 | 0.8 | 0.24 | 0.02 |
| Set 3 | Ex 1I | Polymer 2 | 1 190 000 | 0.28 [b] | 1.37 | 0.8 | 0.17 | 0.02 |
| | Ex 1J | Polymer 3 | 305 000 | 0.23 [b] | 1.17 | 0.8 | 0.17 | 0.01 |
| | Ex 1K | Polymer 4 | 368 000 | 0.28 [b] | 1.37 | 0.8 | 0.16 | 0.03 |
| Set 4 | Ex 1L | Polymer 1 | 333 000 | 0.25 [b] | 1.25 | 0.5 | 0.23 | 0.02 |
| | Ex 1M | Polymer 4 | 368 000 | 0.28 [b] | 1.37 | 0.5 | 0.20 | 0.05 |
| | Ex 1N (comparative) | Jaguar ® C14s | 2 000 000 | 0.13 [b] | 0.72 | 0.5 | 0.37 | 0.01 |
| | Ex 1O (comparative) | Ucare ® JR400 | 450 000 | — | 1.3 [a] | 0.5 | 0.20 | 0.03 |

[a] Literature data
[b] The degree of cationic substitution is calculated after an acidic methanol extraction and thus corresponds to a (DScat)extraction.

From the first set of measurements, it comes out that the shampoo formulation containing polymer 1 (example 1C) provides good wet comb improvement versus the polymer-free formulation (example 1A) and good dry hair look, contrary to comparative formulation comprising Jaguar® C500 (example 1B) which provides low wet comb improvement and formulation comprising Jaguar® C17 (example 1D) which provides good wet comb improvement but unacceptable dry hair look (FIG. 1).

The second set of measurements shows that polymer 3 (example 1G) is at least as good as polymer 1 (example 1F) and provides significant improvement versus Jaguar® C14 s (example 1H).

The third set of measurements shows that polymer 2 and polymer 4 also provide good wet combing performance as the wet combing work for these polymers is similar to the one achieved with polymer 3.

| Ingredients | Parts by weight active % |
|---|---|
| Sodium Laureth Sulfate | 14 |
| Cocamidopropyl Betaine | 2 |
| Cationic Polymer | 0.2 |
| Dimethicone Emulsion[*] | 1 |
| Sodium Chloride | 1.8 |
| Citric acid to pH 6.0-6.5 | qs |
| Preservative | qs |
| Water | to 100 |

[*]droplet size: approx. 0.75 µm; emulsion prepared using Mirasil DM 500 000 from Bluestar Silicones

TABLE 2

| Set | Example | Cationic polymer | Mw (g/mol) | DS cat | Charge density (meq/g) | Silicone Deposition Yield % | Mean Error % |
|---|---|---|---|---|---|---|---|
| Set 1 | Ex 2A (comparative) | Jaguar ® C500 | 389 000 | 0.13 [b] | 0.72 | 16.9 | 4.2 |
| | Ex 2B (comparative) | Ucare ® JR400 | 450 000 | — | 1.3 [a] | 6.7 | 0.7 |
| | Ex 2C (comparative) | Ucare ® JR30M | 2 000 000 | — | 1.3 [a] | 19.9 | 1.2 |
| | Ex 2D (comparative) | Jaguar ® C13s | 2 000 000 | 0.13 [b] | 0.72 | 35.8 | 0.4 |
| | Ex 2E | Polymer 1 | 333 000 | 0.25 [b] | 1.25 | 37.1 | 1.7 |
| Set 2 | Ex 2F | Polymer 1 | 333 000 | 0.25 [b] | 1.25 | 37.1 | 1.9 |
| | Ex 2G | Polymer 3 | 305 000 | 0.23 [b] | 1.17 | 35.3 | 0.4 |
| Set 3 | Ex 2H | Polymer 2 | 1 190 000 | 0.28 [b] | 1.37 | 45.6 | 0.2 |
| | Ex 2I | Polymer 3 | 305 000 | 0.23 [b] | 1.17 | 35.3 | 0.5 |
| Set 4 | Ex 2J | Polymer 1 | 333 000 | 0.25 [b] | 1.25 | 37.1 | 0.8 |
| | Ex 2K | Polymer 4 | 368 000 | 0.28 [b] | 1.37 | 27.7 | 0.4 |

[a] Literature data
[b] The degree of cationic substitution is calculated after an acidic methanol extraction and thus corresponds to a (DScat)extraction.

The first set of measurements shows that the shampoo formulation containing polymer 1 (example 2E) provides good silicone deposition efficiency (similar deposition yield to the one of Jaguar® C13 s), contrary to the shampoo formulations based on Ucare® JR400 (example 2B), Ucare® JR30M (example 2C) and Jaguar® C500 (example 2A) for which the deposition yield is below 20%.

The second set of measurements shows that polymer 3 (example 2G) provides the same deposition efficiency as polymer 1 (example 2F), The third set of measurements shows that polymer 2 (example 2H) even provides higher silicone deposition efficiency than polymer 3 (example 2I) very likely because of its higher molecular weight.

The fourth set of measurements shows that polymer 4 provides lower silicone deposition efficiency than polymer 1 but it stills outperforms the deposition yields achieved with Ucare® JR400 (example 2B), Ucare® JR30M (example 2C) and Jaguar® C500 (example 2A).

Hence, the use of the polymers of the invention in a hair composition allows both providing high conditioning benefits (low combing work, high silicone deposition efficiency) with no negatives on hair appearance.

F. Examples of Personal Care Compositions Prepared with Polymer 1

The following products whose compositions are given below were prepared. The starting materials used are identified by the INCI names and/or by the commercial references. The amounts indicated are given as active materials.

1) Shampoo and/or Shower Gel Compositions

| Constituents | compositions | | | | | | | |
|---|---|---|---|---|---|---|---|---|
| | 1 | 2 | 3 | 4 | 5 | 6 | 7 | 8 |
| Sodium Lauryl Ether Sulfate (2 EO) Rhodapex ® ES-2K (Rhodia) | 14% | 14% | 10% | 10% | 14% | 14% | 10% | 12% |
| Cocamidopropyl Betaine Mirataine ® BET C-30 (Rhodia) | 2% | 2% | 2% | 2% | 2% | 2% | 2% | 3% |
| 0.6 µm Dimethicone emulsion from Mirasil ® DM 500 000 (Bluestar Silicones) | 1% | 1% | 1% | 1% | 1% | 1% | 1% | 1% |
| Polymer 1 | 0.2% | 0.3% | 0.2% | 0.3% | 0.2% | 0.3% | 0.2% | 0.3% |
| Sodium chloride | 0% | 0% | 0% | 0% | 0.1% | 0.5% | 0.1% | 0% |
| Sodium hydroxide | 0.2% | 0.2% | 0.2% | 0.2% | 0.2% | 0.2% | 0.2% | 0.2% |
| Acrylate/C$_{10-30}$ Alkyl Acrylate Crosspolymer Carbopol ® ETD-2020 (Noveon) | 1% | 1% | 1% | 1% | — | — | — | — |
| Acrylate Copolymer Carbopol ® Aqua SF-1 (Noveon) | — | — | — | — | 1.5% | 1.5% | 1.5% | — |
| Carbomer Carbopol ® 980 (Noveon) | — | — | — | — | — | — | — | 1.2% |
| Glycerol | — | 1% | — | 1% | — | 0.5% | — | 0.5% |
| Glycol Distearate, Laureth-4, Cocamidopropyl Betaine Euperlan ® PK-3000 AM (Cognis) | — | — | 1.5% | — | — | 1.5% | — | 1.5% |
| Glycol Distearate, Laureth-7, Sodium Cocoamphoacetate, Cocamidopropyl Betaine, Sodium Laureth Sulfate Mirasheen ® CP-820/G (Rhodia) | — | — | — | 2% | — | — | 2% | — |

-continued

|  | compositions | | | | | | | |
|---|---|---|---|---|---|---|---|---|
| Constituents | 1 | 2 | 3 | 4 | 5 | 6 | 7 | 8 |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

2) Shampoo and/or Shower Gel Compositions

|  | Compositions | | | | | | | |
|---|---|---|---|---|---|---|---|---|
| Constituents | 9 | 10 | 11 | 12 | 13 | 14 | 15 | 16 |
| Sodium Lauryl Ether Sulfate (2 EO) Rhodapex ® ES-2K (Rhodia) | 14% | 11% | 10% | 10% | 12% | 12% | 10% | 10% |
| Coco Betaine Mackam ® CB-35 (Rhodia) | 2% | — | 3% | — | — | 4% | 3% | — |
| Disodium Cocoamphodiacetate Miranol ® C2M Conc NP (Rhodia) | — | 3% | — | 3% | 4% | — | — | 2% |
| 0.6 µm Dimethicone emulsion from Mirasil ® DM 500 000 (Bluestar Silicones) | 1% | 1% | 1% | 1% | 1% | 1% | 1% | 1% |
| Polymer 1 | 0.2% | 0.2% | 0.2% | 0.2% | 0.2% | 0.2% | 0.2% | 0.2% |
| Sodium chloride | — | — | 0.5% | 0.5% | — | — | — | 1.8% |
| Sodium hydroxide | — | — | — | — | — | — | 0.5% | — |
| PEG-200 Hydrogenated Glyceryl Palmate Rewoderm ® LI 520-70 (Evonik) | 0.7% | 1.2% | — | — | 0.5% | — | — | — |
| PEG-150 Distearate Rewopal ® PEG-6000 DS (Evonik) | — | — | — | — | — | 1% | 0.4% | — |
| Xanthan gum Rhodicare ® XC (Rhodia) | — | — | 0.6% | 0.6% | 0.6% | — | — | — |
| Hydroxyethyl cellulose Natrosol ® 250-HHR HEC (Aqualon) | — | — | — | — | — | — | 1% | — |
| Hydroxypropyl Guar Jaguar ® HP-105 (Rhodia) | — | — | — | — | — | — | — | 0.8% |
| Propylene Glycol | 0.3% | 0.3% | — | — | — | 0.4% | 0.3% | 0.3% |
| Glycol Distearate, Laureth-4, Cocamidopropyl Betaine Euperlan ® PK-3000 AM (Cognis) | 1.5% | — | 1.5% | — | — | 1.5% | — | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

3) Shampoo and/or Shower Gel Compositions

|  | Compositions | | | | | | | |
|---|---|---|---|---|---|---|---|---|
| Constituents | 17 | 18 | 19 | 20 | 21 | 22 | 23 | 24 |
| Sodium Lauryl Ether Sulfate (2 EO) Rhodapex ® ES-2K (Rhodia) | 14% | 11% | 10% | 10% | 12% | 12% | 10% | 10% |
| Disodium Cocoamphodiacetate Miranol ® C2M Conc NP (Rhodia) | 2% | 3% | 2% | 3% | 4% | 2% | 2% | 2% |
| 0.6 µm Dimethicone emulsion from Mirasil ® DM 500 000 (Bluestar Silicones) | 1% | 1% | 1% | 1% | 1% | 1% | 1% | 1% |
| Polymer 1 | 0.2% | 0.2% | 0.2% | 0.2% | 0.2% | 0.2% | 0.2% | 0.2% |
| Sodium chloride | 0.2% | 0.15% | 0.1% | 0.15% | 0.15% | 0.15% | 0.15% | 0.15% |
| Sodium hydroxide | 0.2% | 0.2% | 0.2% | 0.2% | 0.2% | 0.2% | 0.2% | 0.2% |
| Acrylate/$C_{10-30}$ Alkyl Acrylate Crosspolymer Carbopol ® ETD-2020 (Noveon) | 1% | 1% | 1% | 1% | 1% | 1% | 1% | 1% |

-continued

| Constituents | Compositions | | | | | | | |
|---|---|---|---|---|---|---|---|---|
| | 17 | 18 | 19 | 20 | 21 | 22 | 23 | 24 |
| Guar Hydroxypropyltrimonium Chloride Jaguar ® C-13S (Rhodia) | 0.1% | — | — | — | — | — | — | — |
| Guar Hydroxypropyltrimonium Chloride Jaguar ® Excel (Rhodia) | — | 0.1% | — | 0.1% | — | — | — | — |
| Hydroxypropyl Guar Hydroxypropyltrimonium Chloride Jaguar ® C-162 (Rhodia) | — | — | 0.3% | — | — | — | — | — |
| Polyquaternium-10 Ucare Polymer ® JR-400 (Amerchol) | — | — | — | 0.1% | 0.3% | — | — | — |
| Polyquaternium-7 Merquat ® 550 (Nalco) | — | — | — | — | — | 0.3% | — | — |
| Polyquaternium-11 Mirapol ® PQ-11 (Rhodia) | — | — | — | — | — | — | 0.05% | — |
| Polyquaternium-22 Merquat ® 280 (Nalco) | — | — | — | — | — | — | — | 0.1% |
| Glycol Distearate, Laureth-4, Cocamidopropyl Betaine Euperlan ® PK-3000 AM (Cognis) | 1.5% | — | — | — | 1.5% | — | 1.5% | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

4) Shampoo and/or Shower Gel Compositions

| Constituents | Compositions | | | | | | | |
|---|---|---|---|---|---|---|---|---|
| | 25 | 26 | 27 | 28 | 29 | 30 | 31 | 32 |
| Anionic surfactant: Sodium Lauryl Ether Sulfate (2 EO) Rhodapex ® ES-2K (Rhodia) | 14% | 11% | 10% | 10% | 12% | 12% | 10% | 10% |
| Cocamidopropyl Betaine Mirataine ® BET C-30 (Rhodia) | 2% | — | 3% | — | — | 4% | 3% | 3% |
| 0.6 µm Dimethicone emulsion from Mirasil ® DM 500 000 (Bluestar Silicones) | 1% | 1% | 1% | 1% | 1% | 1% | 1% | 1% |
| Polymer 1 | 0.2% | 0.2% | 0.2% | 0.2% | 0.2% | 0.2% | 0.2% | 0.2% |
| Sodium chloride | 0.1% | 0.1% | 0.1% | — | 0.1% | — | — | — |
| Acrylate Copolymer Carbopol ® Aqua SF-1 (Noveon) | 1.5% | 1.5% | 1.5% | 1.5% | 1.5% | 1.5% | 1.5% | 1.5% |
| Sodium hydroxide | 0.2% | 0.2% | 0.2% | 0.2% | 0.2% | 0.2% | 0.2% | 0.2% |
| Guar Hydroxypropyltrimonium Chloride Jaguar ® C-13S (Rhodia) | 0.1% | — | — | 0.1% | — | — | — | — |
| Polyquaternium-10 Ucare Polymer ® JR-400 (Amerchol) | — | 0.3% | — | — | — | — | — | — |
| Polyquaternium-39 Merquat ® Plus 3330 (Nalco) | — | — | 0.3% | — | — | — | — | — |
| Polyquaternium-44 Luviquat ® UltraCare (BASF) | — | — | — | 0.1% | 0.1% | — | — | — |
| Polyquaternium-67 SoftCAT ® Polymer SL (Amerchol) | — | — | — | — | — | 0.2% | — | — |
| Polymethacrylamidopropyltrimonium Chloride Polycare 133 (Rhodia) | — | — | — | — | — | — | 0.2% | — |
| Acrylamidopropyltrimonium Chloride/ Acrylamide Copolymer Salcare ® SC-60 (Ciba SC) | — | — | — | — | — | — | — | 0.3% |
| Glycol Distearate, Laureth-4, Cocamidopropyl Betaine Euperlan ® PK-3000 AM (Cognis) | 1.5% | 1.5% | 1.5% | 1.5% | 1.5% | 1.5% | 1.5% | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

5) Shampoo and/or Gel Compositions

| Constituents | Compositions | | | | | | | |
|---|---|---|---|---|---|---|---|---|
| | 33 | 34 | 35 | 36 | 37 | 38 | 39 | 40 |
| Sodium Lauryl Ether Sulfate (2 EO) Rhodapex ® ES-2K (Rhodia) | — | 14% | 14% | — | 14% | — | — | 14% |
| Ammonium Lauryl Ether Sulfate (2 EO) Rhodapex ® EA-2 (Rhodia) | 14% | — | — | 14% | — | 14% | 14% | — |
| Disodium Cocoamphodiacetate Miranol ® C2M Conc NP (Rhodia) | 2% | 1.5% | 1.5% | 2% | 1.5% | 2% | 2% | 1.5% |
| 0.6 µm Dimethicone emulsion from Mirasil ® DM-500,000 (Bluestar Silicones) | 1% | — | — | — | — | — | — | — |
| 0.9 µm Dimethicone emulsion from Mirasil ® DM-500,000 (Bluestar Silicones) | — | 1% | — | — | — | — | — | — |
| 2 µm Dimethicone emulsion: Mirasil ® DME-2 (Bluestar Silicones) | — | — | 1% | — | — | — | — | — |
| 30 µm Dimethicone emulsion: Mirasil ® DME-30 (Bluestar Silicones) | — | — | — | 1% | — | — | — | — |
| Amodimethicone Dow Corning ® 2-8566 Amino Fluid (Dow Corning) | — | — | — | — | 1% | — | — | — |
| Dimethiconol emulsion: Dow Corning ® 1501 (Dow Corning) | — | — | — | — | — | 1% | — | — |
| Divinyldimethicone/dimethicone copolymer emulsion: Dow Corning ® HMW 2220 (Dow Corning) | — | — | — | — | — | — | 1% | — |
| PEG/PPG-10/2 Dimethicone: Mirasil ® DMCP-93 (Rhodia) | — | — | — | — | — | — | — | 1% |
| Polymer 1 | 0.2% | 0.2% | 0.2% | 0.2% | 0.2% | 0.2% | 0.2% | 0.2% |
| Sodium hydroxide | 0.2% | 0.2% | 0.2% | 0.2% | — | 0.2% | 0.2% | — |
| Sodium chloride | 0.1% | 0.1% | 0.2% | 0.1% | 1% | 0.3% | 0.1% | 1.8% |
| Acrylate Copolymer Carbopol ® Aqua SF-1 (Noveon) | 1.5% | 1.5% | — | 2% | — | — | 1.8% | — |
| Carbomer Carbopol ® 980 (Noveon) | — | — | 1.2% | — | — | 1% | — | — |
| Glycol Distearate, Laureth-4, Cocamidopropyl Betaine Euperlan ® PK-3000 AM (Cognis) | — | — | — | 1.5% | — | 1.5% | — | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

6) Shampoo and/or Shower Gel Compositions

| Constituents | Compositions | | | | | | | |
|---|---|---|---|---|---|---|---|---|
| | 41 | 42 | 43 | 44 | 45 | 46 | 47 | 48 |
| Sodium Lauryl Ether Sulfate (2 EO) Rhodapex ® ES-2K (Rhodia) | — | 10% | 6% | — | 12% | 12% | — | 14% |
| Ammonium Lauryl Sulfate Rhodapon ® ALSA/K | 5% | — | 6% | 7% | — | — | 5% | — |
| Ammonium Lauryl Ether Sulfate (2 EO) Rhodapex ® EA-2 (Rhodia) | — | — | — | 7% | — | — | 7% | — |
| Disodium Cocoamphodiacetate Miranol ® C2M Conc NP (Rhodia) | 3% | — | — | — | — | 3% | — | 1% |
| Cocamidopropyl Betaine Mirataine ® BET C-30 (Rhodia) | — | 4% | — | — | 3% | — | 2% | 2% |
| Disodium Laureth Sulfosuccinate Mackanate ® EL (Rhodia) | 6% | — | 2% | — | 2% | — | — | — |
| Sodium Lauroyl Glutamate Protelan ® AGL-95 (Zschimmer & Schwarz) | — | 2% | — | — | — | — | — | 2% |
| Coco Glucoside Plantacare ® 818 UP (Cognis) | 2% | — | — | 1% | — | 2% | — | — |
| Cocamide MIPA Mackamide ® (Rhodia) | 1% | — | 1.5% | — | 1% | — | 1% | 1% |
| Laureth-2 Empilan ® KBE-2 (Huntsman) | — | 1% | — | — | — | — | — | — |

-continued

| Constituents | Compositions | | | | | | | |
|---|---|---|---|---|---|---|---|---|
| | 41 | 42 | 43 | 44 | 45 | 46 | 47 | 48 |
| Sodium Lauroyl Sarcosinate Protelan ® LS-9011 (Zschimmer & Schwarz) | — | — | — | 1% | — | — | 2% | — |
| 0.6 μm Dimethicone emulsion: Mirasil ® DM-500,000 (Bluestar Silicones) | 1% | 1% | 1% | 1% | 1% | 1% | 1% | 1% |
| Polymer 1 | 0.2% | 0.2% | 0.2% | 0.2% | 0.2% | 0.2% | 0.2% | 0.2% |
| Sodium hydroxide | 0.2% | 0.2% | 0.2% | 0.2% | — | 0.2% | 0.2% | — |
| Sodium chloride | 0.1% | 0.1% | 0.2% | 0.1% | 1.6% | 0.3% | 0.1% | 1.2% |
| Acrylate/$C_{10-30}$ Alkyl Acrylate Crosspolymer Carbopol ® ETD-2020 (Noveon) | 1% | 1% | 1% | 1% | — | — | — | — |
| Acrylate Copolymer Carbopol ® Aqua SF-1 (Noveon) | — | — | — | — | 1.5% | 1.5% | 1.5% | 1.5% |
| Glycol Distearate, Laureth-4, Cocamidopropyl Betaine Euperlan ® PK-3000 AM (Cognis) | — | — | — | 1.5% | — | 1.5% | — | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

7) Shampoo and/or Shower Gel Compositions

| Constituents | Compositions | | | | | | | |
|---|---|---|---|---|---|---|---|---|
| | 49 | 50 | 51 | 52 | 53 | 54 | 55 | 56 |
| Sodium Lauryl Ether Sulfate (2 EO) Rhodapex ® ES-2K (Rhodia) | — | 14% | 14% | — | 14% | — | — | 14% |
| Ammonium Lauryl Ether Sulfate (2 EO) Rhodapex ® EA-2 (Rhodia) | 14% | — | — | 14% | — | 14% | 14% | — |
| Disodium Cocoamphodiacetate Miranol ® C2M Conc NP (Rhodia) | 2% | 1.5% | 1.5% | 2% | 1.5% | 2% | 2% | 1.5% |
| Cocamide MIPA Mackamide ® CPA (Rhodia) | 1% | 1% | 1% | 1% | 1% | 1% | 1% | 1% |
| Cetrimonium Chloride Fentacare ® 1631 (Rhodia) | 1% | — | — | — | — | — | — | — |
| Zinc Pyrithione Zinc Omadine ® (Arch Chemical) | — | 1% | — | — | — | — | — | — |
| Piroctone Olamine Octopirox ® (Clariant) | — | — | 1% | — | — | — | — | — |
| Selenium sulfide | — | — | — | 1% | — | — | — | — |
| Salicylic acid (Rhodia) | — | — | — | — | 1% | — | — | — |
| Benzophenone-3 Uvinul ® M-40 (BASF) | — | — | — | — | — | 1% | — | — |
| Ethylhexyl Methoxycinnamate Parsol ® MCX (DSM) | — | — | — | — | — | — | 1% | — |
| Polysilicone-15 Parsol ® SLX (DSM) | — | — | — | — | — | — | — | 1% |
| Polymer 1 | 0.2% | 0.2% | 0.2% | 0.2% | 0.2% | 0.2% | 0.2% | 0.2% |
| Sodium hydroxide | — | 0.1% | 0.1% | 0.1% | 0.1% | 0.1% | 0.1% | 0.1% |
| Sodium chloride | 1.1% | 0.1% | 0.2% | 0.1% | 0.2% | 0.3% | 0.1% | 0.1% |
| Acrylate Copolymer Carbopol ® Aqua SF-1 (Noveon) | — | 0.8% | 0.7% | 0.7% | 0.7% | — | — | — |
| Carbomer Carbopol ® 980 (Noveon) | — | — | — | — | — | 0.5% | 0.5% | 0.5% |
| Glycol Distearate, Laureth-4, Cocamidopropyl Betaine Euperlan ® PK-3000 AM (Cognis) | — | — | — | 1.5% | — | 1.5% | — | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

8) Shampoo and/or Shower Gel Compositions

| Constituents | 57 | 58 | 59 | 60 | 61 |
|---|---|---|---|---|---|
| Sodium Lauryl Ether Sulfate (2 EO) Rhodapex ® ES-2K (Rhodia) | 10% | 10% | 14% | 10% | 12% |
| Cocamidopropyl Betaine Mirataine ® BET C-30 (Rhodia) | 2% | 2% | 2% | 2% | 3% |
| 0.6 µm Dimethicone emulsion from Mirasil ® DM-500,000 (Bluestar Silicones) | 1% | 1% | 1% | 1% | 1% |
| Polymer 1 | 0.2% | 0.3% | 0.3% | 0.2% | 0.3% |
| Sodium chloride | 0% | 0% | 0.5% | 0.1% | 0% |
| Sodium hydroxide | 0.2% | 0.2% | 0.2% | 0.2% | 0.2% |
| Acrylate/$C_{10-30}$ Alkyl Acrylate Crosspolymer Carbopol ® ETD-2020 (Noveon) | 1% | 1% | — | — | — |
| Acrylate Copolymer Carbopol ® Aqua SF-1 (Noveon) | — | — | 1.5% | 1.5% | — |
| Carbomer Carbopol ® 980 (Noveon) | — | — | — | — | 1.2% |
| Glycerol | — | 1% | 0.5% | — | 0.5% |
| Sodium Laureth Sulfate, Glycol Distearate Cocamide MEA, Laureth-10 Euperlan PK-771 BENZ (Cognis) | 1.5% | — | 1.5% | — | 1.5% |
| PEG-3 Distearate Genapol TS (Clariant) | — | 1.5% | — | 1.5% | — |
| Citric acid | qs | qs | qs | qs | qs |
| Fragrance, preserving agents | qs | qs | qs | qs | qs |
| Demineralized water | qsp 100% | qsp 100% | qsp 100% | qsp 100% | qsp 100% |

9) SHAMPOO AND/OR SHOWER GEL COMPOSITIONS

| Constituents | 62 | 63 | 64 | 65 | 66 | 67 | 68 | 69 |
|---|---|---|---|---|---|---|---|---|
| Sodium Lauryl Ether Sulfate (2 EO) Rhodapex ® ES-2K (Rhodia) | 14% | 10% | 12% | 10% | 14% | 10% | 12% | 10% |
| Coco Betaine Mirataine ® BB-FLA (Rhodia) | 2% | 3% | 4% | — | 2% | 3% | 4% | — |
| Disodium Cocoamphodiacetate Miranol ® C2M Conc NP (Rhodia) | — | — | — | 2% | — | — | — | 2% |
| 0.6 µm Dimethicone emulsion from Mirasil ® DM-500,000 (Bluestar Silicones) | 1% | 1% | 1% | 1% | 1% | 1% | 1% | 1% |
| Polymer 1 | 0.2% | 0.2% | 0.2% | 0.2% | 0.2% | 0.2% | 0.2% | 0.2% |
| Sodium chloride | — | 0.5% | — | 1.8% | — | 0.5% | — | 1.8% |
| Sodium hydroxide | — | — | — | — | — | — | — | — |
| PEG-200 Hydrogenated Glyceryl Palmate Rewoderm ® LI 520-70 (Evonik) | 0.7% | — | — | — | 0.7% | — | — | — |
| PEG-150 Distearate Rewopal ® PEG-6000 DS (Evonik) | — | — | 1% | — | — | — | 1% | — |
| Xanthan gum Rhodicare ® XC (Rhodia) | — | 0.6% | — | — | — | 0.6% | — | — |
| Hydroxyethyl cellulose Natrosol ® 250-HHR HEC (Aqualon) | — | — | — | — | — | — | — | — |
| Hydroxypropyl Guar Jaguar ® HP-105 (Rhodia) | — | — | — | 0.8% | — | — | — | 0.8% |
| Propylene Glycol | 0.3% | — | 0.4% | 0.3% | 0.3% | — | 0.4% | 0.3% |
| Sodium Laureth Sulfate, Glycol Distearate Cocamide MEA, Laureth-10 Euperlan PK-771 BENZ (Cognis) | 1.0% | 1.0% | 1.0% | 1.0% | — | — | — | — |
| PEG-3 Distearate Genapol TS (Clariant) | — | — | — | — | 1.5% | 1.5% | 1.5% | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

10) Shampoo and/or Shower Gel Compositions

| Constituents | Compositions | | | | | | | |
|---|---|---|---|---|---|---|---|---|
| | 70 | 71 | 72 | 73 | 74 | 75 | 76 | 77 |
| Sodium Lauryl Ether Sulfate (2 EO) Rhodapex ES-2K (Rhodia) | 14% | 12% | 10% | 10% | 14% | 12% | 10% | 10% |
| Disodium Cocoamphodiacetate Miranol ® C2M Conc NP (Rhodia) | 2% | 4% | 2% | 2% | 2% | 4% | 2% | 2% |
| 0.6 μm Dimethicone emulsion from Mirasil ® DM-500,000 (Bluestar Silicones) | 1% | 1% | 1% | 1% | 1% | 1% | 1% | 1% |
| Polymer 1 | 0.2% | 0.2% | 0.2% | 0.2% | 0.2% | 0.2% | 0.2% | 0.2% |
| Sodium chloride | 0.2% | 0.15% | 0.15% | 0.15% | 0.2% | 0.15% | 0.15% | 0.15% |
| Sodium hydroxide | 0.2% | 0.2% | 0.2% | 0.2% | 0.2% | 0.2% | 0.2% | 0.2% |
| Acrylate/$C_{10-30}$ Alkyl Acrylate Crosspolymer Carbopol ® ETD-2020 (Noveon) | 1% | 1% | 1% | 1% | 1% | 1% | 1% | 1% |
| Guar Hydroxypropyltrimonium Chloride Jaguar ® C-13S (Rhodia) | 0.1% | — | — | — | 0.1% | — | — | — |
| Guar Hydroxypropyltrimonium Chloride Jaguar ® Excel (Rhodia) | — | — | — | — | — | — | — | — |
| Hydroxypropyl Guar Hydroxypropyltrimonium Chloride Jaguar ® C-162 (Rhodia) | — | — | — | — | — | — | — | — |
| Polyquaternium-10 Ucare Polymer ® JR-400 (Amerchol) | — | 0.3% | — | — | — | 0.3% | — | — |
| Polyquaternium-7 Merquat ® 550 (Nalco) | — | — | — | — | — | — | — | — |
| Polyquaternium-11 Mirapol ® PQ-11 (Rhodia) | — | — | 0.05% | — | — | — | 0.05% | — |
| Polyquaternium-22 Merquat ® 280 (Nalco) | — | — | — | 0.1% | — | — | — | 0.1% |
| Sodium Laureth Sulfate, Glycol Distearate Cocamide MEA, Laureth-10 Euperlan PK-771 BENZ (Cognis) | 1.5% | 1.5% | 1.5% | 1.5% | — | — | — | — |
| PEG-3 Distearate Genapol TS (Clariant) | — | — | — | — | 1.5% | 1.5% | 1.5% | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

11) Shampoo and/or Shower Gel Compositions

| Constituents | Compositions | | | | | | | |
|---|---|---|---|---|---|---|---|---|
| | 78 | 79 | 80 | 81 | 82 | 83 | 84 | 85 |
| Anionic surfactant: Sodium Lauryl Ether Sulfate (2 EO) Rhodapex ES-2K (Rhodia) | 14% | 11% | 10% | 10% | 12% | 12% | 10% | 10% |
| Cocamidopropyl Betaine Mirataine ® BET C-30 (Rhodia) | 2% | — | 3% | — | — | 4% | 3% | 3% |
| 0.6 μm Dimethicone emulsion from Mirasil ® DM-500,000 (Bluestar Silicones) | 1% | 1% | 1% | 1% | 1% | 1% | 1% | 1% |
| Polymer 1 | 0.2% | 0.2% | 0.2% | 0.2% | 0.2% | 0.2% | 0.2% | 0.2% |
| Sodium chloride | 0.1% | 0.1% | 0.1% | — | 0.1% | — | — | — |
| Acrylate Copolymer Carbopol ® Aqua SF-1 (Noveon) | 1.5% | 1.5% | 1.5% | 1.5% | 1.5% | 1.5% | 1.5% | 1.5% |
| Sodium hydroxide | 0.2% | 0.2% | 0.2% | 0.2% | 0.2% | 0.2% | 0.2% | 0.2% |
| Guar Hydroxypropyltrimonium Chloride Jaguar ® C-13S (Rhodia) | 0.1% | — | — | 0.1% | — | — | — | — |

-continued

| Constituents | 78 | 79 | 80 | 81 | 82 | 83 | 84 | 85 |
|---|---|---|---|---|---|---|---|---|
| Polyquaternium-10 Ucare Polymer ® JR-400 (Amerchol) | — | 0.3% | — | — | — | — | — | — |
| Polyquaternium-39 Merquat ® Plus 3330 (Nalco) | — | — | 0.3% | — | — | — | — | — |
| Polyquaternium-44 Luviquat ® UltraCare (BASF) | — | — | — | 0.1% | 0.1% | — | — | — |
| Polyquaternium-67 SoftCAT ® Polymer SL (Amerchol) | — | — | — | — | — | 0.2% | — | — |
| Polymethacrylamidopropyltrimonium Chloride Polycare 133 (Rhodia) | — | — | — | — | — | — | 0.2% | — |
| Acrylamidopropyltrimonium Chloride/Acrylamide Copolymer Salcare ® SC-60 (Ciba SC) | — | — | — | — | — | — | — | 0.3% |
| Sodium Laureth Sulfate, Glycol distearate Cocamide MEA, Laureth-10 Euperlan PK-771 BENZ (Cognis) | 1.5% | 1.5% | 1.5% | 1.5% | 1.5% | 1.5% | 1.5% | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

12) Shampoo and/or Shower Gel Compositions

| Constituents | 86 | 87 | 88 | 89 | 90 | 91 | 92 | 93 |
|---|---|---|---|---|---|---|---|---|
| Anionic surfactant: Sodium Lauryl Ether Sulfate (2 EO) Rhodapex ES-2K (Rhodia) | 14% | 11% | 10% | 10% | 12% | 12% | 10% | 10% |
| Cocamidopropyl Betaine Mirataine ® BET C-30 (Rhodia) | 2% | — | 3% | — | — | 4% | 3% | 3% |
| 0.6 μm Dimethicone emulsion from Mirasil ® DM-500,000 (Bluestar Silicones) | 1% | 1% | 1% | 1% | 1% | 1% | 1% | 1% |
| Polymer 1 | 0.2% | 0.2% | 0.2% | 0.2% | 0.2% | 0.2% | 0.2% | 0.2% |
| Sodium chloride | 0.1% | 0.1% | 0.1% | — | 0.1% | — | — | — |
| Acrylate Copolymer Carbopol ® Aqua SF-1 (Noveon) | 1.5% | 1.5% | 1.5% | 1.5% | 1.5% | 1.5% | 1.5% | 1.5% |
| Sodium hydroxide | 0.2% | 0.2% | 0.2% | 0.2% | 0.2% | 0.2% | 0.2% | 0.2% |
| Guar Hydroxypropyltrimonium Chloride Jaguar ® C-13S (Rhodia) | 0.1% | — | — | 0.1% | — | — | — | — |
| Polyquaternium-10 Ucare Polymer ® JR-400 (Amerchol) | — | 0.3% | — | — | — | — | — | — |
| Polyquaternium-39 Merquat ® Plus 3330 (Nalco) | — | — | 0.3% | — | — | — | — | — |
| Polyquaternium-44 Luviquat ® UltraCare (BASF) | — | — | — | 0.1% | 0.1% | — | — | — |
| Polyquaternium-67 SoftCAT ® Polymer SL (Amerchol) | — | — | — | — | — | 0.2% | — | — |
| Polymethacrylamidopropyltrimonium Chloride Polycare 133 (Rhodia) | — | — | — | — | — | — | 0.2% | — |
| Acrylamidopropyltrimonium Chloride/Acrylamide Copolymer Salcare ® SC-60 (Ciba SC) | — | — | — | — | — | — | — | 0.3% |
| PEG-3 Distearate Genapol TS (Clariant) | 1.5% | 1.5% | 1.5% | 1.5% | 1.5% | 1.5% | 1.5% | 1.5% |
| Citric acid | qs | qs | qs | qs | qs | qs | qs | qs |
| Fragrance, preserving agents | qs | qs | qs | qs | qs | qs | qs | qs |
| Demineralized water | qsp 100% | qsp 100% | qsp 100% | qsp 100% | qsp 100% | qsp 100% | qsp 100% | qsp 100% |

13) Shampoo and/or Shower Gel Compositions

| Constituents | Compositions | | | | | |
|---|---|---|---|---|---|---|
| | 94 | 95 | 96 | 97 | 98 | 99 |
| Sodium Lauryl Ether Sulfate (2 EO) Rhodapex ES-2K (Rhodia) | — | — | 14% | — | — | 14% |
| Ammonium Lauryl Ether Sulfate (2 EO) Rhodapex ® EA-2 (Rhodia) | 14% | 14% | — | 14% | 14% | — |
| Disodium Cocoamphodiacetate Miranol ® C2M Conc NP (Rhodia) | 2% | 2% | 1.5% | 2% | 2% | 1.5% |
| 0.6 μm Dimethicone emulsion from Mirasil ® DM-500,000 (Bluestar Silicones) | — | — | — | — | — | — |
| 0.9 μm Dimethicone emulsion: Mirasil ® DM-500,000 (Bluestar Silicones) | — | — | — | — | — | — |
| 2 μm Dimethicone emulsion: Mirasil ® DME-2 (Bluestar Silicones) | — | — | — | — | — | — |
| 30 μm Dimethicone emulsion: Mirasil (Bluestar Silicones) | 1% | — | — | 1% | — | — |
| Amodimethicone Dow Corning ® 2-8566 Amino Fluid (Dow Corning) | — | — | — | — | — | — |
| Dimethiconol emulsion: Dow Corning ® 1501 (Dow Corning) | — | 1% | — | — | 1% | — |
| Divinyldimethicone/dimethicone copolymer emulsion: Dow Corning ® HMW 2220 (Dow Corning) | — | — | — | — | — | — |
| PEG/PPG-10/2 Dimethicone: Mirasil ® DMCP-93 (Rhodia) | — | — | 1% | — | — | 1% |
| Polymer 1 | 0.2% | 0.2% | 0.2% | 0.2% | 0.2% | 0.2% |
| Sodium hydroxide | 0.2% | 0.2% | — | 0.2% | 0.2% | — |
| Sodium chloride | 0.1% | 0.3% | 1.8% | 0.1% | 0.3% | 1.8% |
| Acrylate Copolymer Carbopol ® Aqua SF-1 (Noveon) | 2% | — | — | 2% | — | — |
| Carbomer Carbopol ® 980 (Noveon) | — | 1% | — | — | 1% | — |
| Sodium Laureth Sulfate, Glycol Distearate Cocamide MEA, Laureth-10 Euperlan PK-771 BENZ (Cognis) | 1.5% | 1.5% | 1.5% | — | — | — |
| PEG-3 Distearate Genapol TS (Clariant) | — | — | — | 1.0% | 1.5% | 1.5% |
| Citric acid | qs | qs | qs | qs | qs | qs |
| Fragrance, preserving agents | qs | qs | qs | qs | qs | qs |
| Demineralized water | qsp 100% | qsp 100% | qsp 100% | qsp 100% | qsp 100% | qsp 100% |

14) Shampoo and/or Shower Gel Compositions

| Constituents | Compositions | | | | | |
|---|---|---|---|---|---|---|
| | 100 | 101 | 102 | 103 | 104 | 105 |
| Sodium Lauryl Ether Sulfate (2 EO) Rhodapex ES-2K (Rhodia) | — | 12% | 14% | — | 12% | 14% |
| Ammonium Lauryl Sulfate Rhodapon ® ALSA/K | 7% | — | — | 7% | — | — |
| Ammonium Lauryl Ether Sulfate (2 EO) Rhodapex ® EA-2 (Rhodia) | 7% | — | — | 7% | — | — |
| Disodium Cocoamphodiacetate Miranol ® C2M Conc NP (Rhodia) | — | 3% | 1% | — | 3% | 1% |
| Cocamidopropyl Betaine Mirataine ® BET C-30 (Rhodia) | — | — | 2% | — | — | 2% |
| Disodium Laureth Sulfosuccinate Mackanate ® ELK (Rhodia) | — | — | — | — | — | — |
| Sodium Lauroyl Glutamate Protelan ® AGL-95 (Zschimmer & Schwarz) | — | — | 2% | — | — | 2% |

|   | Compositions | | | | | |
|---|---|---|---|---|---|---|
| Constituents | 100 | 101 | 102 | 103 | 104 | 105 |
| Coco Glucoside Plantacare ® 818 UP (Cognis) | 1% | 2% | — | 1% | 2% | — |
| Cocamide MIPA Empilan ® CIS (Huntsman) | — | — | 1% | — | — | 1% |
| Laureth-2 Empilan ® KBE-2 (Huntsman) | — | — | — | — | — | — |
| Sodium Lauroyl Sarcosinate Protelan ® LS-9011 (Zschimmer & Schwarz) | 1% | — | — | 1% | — | — |
| 0.6 μm Dimethicone emulsion: Mirasil ® DM-500,000 (Bluestar Silicones) | 1% | 1% | 1% | 1% | 1% | 1% |
| Polymer 1 | 0.2% | 0.2% | 0.2% | 0.2% | 0.2% | 0.2% |
| Sodium hydroxide | 0.2% | 0.2% | — | 0.2% | 0.2% | — |
| Sodium chloride | 0.1% | 0.3% | 1.2% | 0.1% | 0.3% | 1.2% |
| Acrylate/$C_{10-30}$ Alkyl Acrylate Crosspolymer Carbopol ® ETD-2020 (Noveon) | 1% | — | — | 1% | — | — |
| Acrylate Copolymer Carbopol ® Aqua SF-1 (Noveon) | — | 1.5% | 1.5% | — | 1.5% | 1.5% |
| Sodium Laureth Sulfate, Glycol Distearate Cocamide MEA, Laureth-10 Euperlan PK-771 BENZ (Cognis) | 1.5% | 1.5% | 1.5% | — | — | — |
| PEG-3 Distearate Genapol TS (Clariant) | — | — | — | 1.5% | 1.5% | 1.5% |
| Citric acid | qs | qs | qs | qs | qs | qs |
| Fragrance, preserving agents | qs | qs | qs | qs | qs | qs |
| Demineralized water | qsp 100% | qsp 100% | qsp 100% | qsp 100% | qsp 100% | qsp 100% |

15) Shampoo and/or Shower Gel Compositions

|   | Compositions | | | | | |
|---|---|---|---|---|---|---|
| Constituents | 106 | 107 | 108 | 109 | 110 | 111 |
| Sodium Lauryl Ether Sulfate (2 EO) Rhodapex ES-2K (Rhodia) | — | — | 14% | — | — | 14% |
| Ammonium Lauryl Ether Sulfate (2 EO) Rhodapex ® EA-2 (Rhodia) | 14% | 14% | — | 14% | 14% | — |
| Disodium Cocoamphodiacetate Miranol ® C2M Conc NP (Rhodia) | 2% | 2% | 1.5% | 2% | 2% | 1.5% |
| Cocamide MIPA Mackamide ® CPA (Rhodia) | 1% | 1% | 1% | 1% | 1% | 1% |
| Cetrimonium chloride Fentacare ® 1631 (Rhodia) | — | — | — | — | — | — |
| Zinc Pyrithione Zinc Omadine ® (Arch Chemical) | — | — | — | — | — | — |
| Piroctone Olamine Octopirox ® (Clariant) | — | — | — | — | — | — |
| Selenium sulfide | 1% | — | — | 1% | — | — |
| Salicylic acid (Rhodia) | — | — | — | — | — | — |
| Benzophenone-3 Uvinul ® M-40 (BASF) | — | 1% | — | — | 1% | — |
| Ethylhexyl Methoxycinnamate Parsol ® MCX (DSM) | — | — | — | — | — | — |
| Polysilicone-15 Parsol ® SLX (DSM) | — | — | 1% | — | — | 1% |
| Polymer 1 | 0.2% | 0.2% | 0.2% | 0.2% | 0.2% | 0.2% |
| Sodium hydroxide | 0.1% | 0.1% | 0.1% | 0.1% | 0.1% | 0.1% |
| Sodium chloride | 0.1% | 0.3% | 0.1% | 0.1% | 0.3% | 0.1% |
| Acrylate Copolymer Carbopol ® Aqua SF-1 (Noveon) | 0.7% | — | — | 0.7% | — | — |
| Carbomer Carbopol ® 980 (Noveon) | — | 0.5% | 0.5% | — | 0.5% | 0.5% |
| Sodium Laureth Sulfate, Glycol Distearate Cocamide MEA, Laureth-10 Euperlan PK-771 BENZ (Cognis) | 1.5% | 1.5% | 1.5% | — | — | — |
| PEG-3 Distearate Genapol TS (Clariant) | — | — | — | 1.5% | 1.5% | 1.5% |
| Citric acid | qs | qs | qs | qs | qs | qs |
| Fragrance, preserving agents | qs | qs | qs | qs | qs | qs |

16) Styling Gels Compositions

| Constituents | 106 | 107 | 108 | 109 | 110 | 111 |
|---|---|---|---|---|---|---|
| Demineralized water | qsp 100% | qsp 100% | qsp 100% | qsp 100% | qsp 100% | qsp 100% |

16) Styling Gels Compositions

| Constituents | 112 | 113 | 114 | 115 | 116 | 117 |
|---|---|---|---|---|---|---|
| Polymer 1 | 2% | 1.5% | 0.1% | 2% | 2% | 1.5% |
| Hydroxypropyl Guar Jaguar ® (Rhodia) | 1.5% | | | | 1.5% | |
| Glycerol | 1% | | | 1% | 1% | |
| Aminomethylpropanol AMP | | | 0.16% | | | |
| Hydroxyethylcellulose Natrosol ® 250 HP (Hercules) | | 0.75% | | | | 0.75% |
| Propylene Glycol | | 1% | 3% | 0.5% | | 1% |
| Panthenol D-Panthenol USP (BASF) | | 0.05% | | | | 0.05% |
| Carbomer | | | 0.2% | | | |
| Glucose | | | 7% | | | |
| Hydroxypropyl Guar Jaguar ® HP105 (Rhodia) | | | | 1.5% | | |
| Polysorbate 20 Alkamuls ® T-20C (Rhodia) | | | | | | 0.1% |
| Fragrance, preserving agents | qs | qs | qs | qs | qs | qs |
| Water | qsp 100% | qsp 100% | qsp 100% | qsp 100% | qsp 100% | qsp 100% |

17) Styling Gels Compositions

| Constituents | Composition 118 |
|---|---|
| Polymer 1 | 5% |
| Oleth-20 Rhodasurf ® ON-870 (Rhodia) | 0.5% |
| Simethicone Mirasil ® SM (Rhodia) | 0.3% |
| Acrylates/Steareth-20 Methacrylates Copolymer Aculyn ® 22 (Dow Corning) | 3.33% |
| Panthenol D-Panthenol USP (BASF) | 0.3% |
| Glycerol | 0.5% |
| NaOH 10% | 2% |
| Fragrance, preserving agents | qs |
| Water | qsp 100% |

18) Styling Gels Compositions

| Constituents | 119 | 120 | 121 | 122 | 123 | 124 |
|---|---|---|---|---|---|---|
| Basic Red 51 306008 Arianor ® Cherry Red (LCW) | 1% | 1% | 1% | 1% | 1% | 1% |
| Polysilicone 15 Parsol ® SLX (DSM) | | | 1% | 1% | | |
| Octyl Methoxycinnamate Eusolex ® 2292 (Merck) | | | | | 1% | 1% |
| Disodium Cocoamphodipropionate Miranol ® C2M-SF (Rhodia) | 3.15% | 3.15% | 3.15% | 3.15% | 3.15% | 3.15% |
| Lauramine Oxide Rhodamox ® LO (Rhodia) | 4.2% | | 4.2% | | 4.2% | |
| Trideceth Carboxamide MEA Amideth ® A-15 (Kao) | 3% | | 3% | | 3% | |
| Acrylates/Aminoacrylates/C10-30 Alkyl PEG-20 Itaconate Copolymer Structure ® PLUS (National Starch) | 2.5% | 2.5% | 2.5% | 2.5% | 2.5% | 2.5% |
| Polymer 1 | 0.5% | 0.5% | 0.5% | 0.5% | 0.5% | 0.5% |
| Lauramine Oxide Incromine ® Oxide L (Croda) | | 4.2% | | 4.2% | | 4.2% |
| PPG-2 Hydroxyethyl Cocamide | | | | | | |

-continued

| Constituents | Composition |  |  |  |  |  |
|---|---|---|---|---|---|---|
|  | 119 | 120 | 121 | 122 | 123 | 124 |
| Promidium ® CO (Croda) |  | 3% |  | 3% |  | 3% |
| Fragrances, preserving agents | qs | qs | qs | qs | qs | qs |
| Water | qsp | qsp | qsp | qsp | qsp | qsp |

19) Coloring Shampoo Compositions

| Constituents | Composition | |
|---|---|---|
|  | 125 | 126 |
| Basic Red 51 | 1% | 1% |
| 306008 Arianor ® Cherry Red (LCW) | | |
| Benzophenone-4 | 1% | 1% |
| Uvinul ® MS40 (BASF) | | |
| Disodium Cocoamphodipropionate | 3.15% | 3.15% |
| Miranol ® C2M-SF (Rhodia) | | |
| Lauramine Oxide | 4.2% | |
| Rhodamox ® LO (Rhodia) | | |
| Trideceth Carboxamide MEA | 3% | |
| Amideth ® A-15 (Kao) | | |
| Acrylates/Aminoacrylates/C10-30 Alkyl PEG-20 Itaconate Copolymer Structure ® PLUS (National Starch) | 2.5% | 2.5% |
| Polymer 1 | 0.5% | 0.5% |
| Lauramine Oxide | | 4.2% |
| Incromine ® Oxide L (Croda) | | |
| PPG-2 Hydroxyethyl Cocamide | | 3% |
| Promidium ® CO (Croda) | | |
| Fragrances, preserving agents | qs | qs |
| Water | qsp | qsp |

20) Hair Conditioners Compositions

| Constituents | Compositions | | | |
|---|---|---|---|---|
|  | 127 | 128 | 129 | 130 |
| Polymer 1 | 0.3% | 0.3% | 0.5% | 0.5% |
| SD Alcohol 40 (Prolabo) | 40% | 40% | 40% | 40% |
| Polyquaternium-2 Mirapol ® A-15 (Rhodia) | 1.5% | 1.5% | | |
| PEG/PPG-22/24 Dimethicone | 1.0% | 1.0% | 1.0% | 1.0% |
| Benzophenone-4 Uvinul ® MS40 (BASF) | 0.5% | | | 0.3% |
| Hydrolyzed Keratin | 0.2% | 0.2% | 0.2% | 0.2% |
| Dimethicone (and) Laureth-8 (and) Succinoglycan Mirasil ® DME-30KCG (Bluestar Silicones) | | | 2% | 2% |
| Dye | | | qs | qs |
| Fragrances, preserving agents | qs | qs | qs | qs |
| Water | qsp | qsp | qsp | qsp |

21) Hair Conditioners Compositions

| Constituents | Compositions | | | | |
|---|---|---|---|---|---|
|  | 131 | 132 | 133 | 134 | 135 |
| Glyceryl Stearate (and) PEG-100 Stearate | 7% | 7% | 4% | 4% | 4% |
| Polymer 1 | 0.2% | 0.2% | 0.2% | 0.2% | 0.2% |
| Cetearyl Alcohol | 6% | 6% | | | |
| Wheat (Triticum vulgare) Germ Oil | 5% | 5% | 4% | 4% | 4% |
| Coconut (Cocos nucifera) Oil | 5% | 5% | | | |
| Mineral oil Marcol ® 82 (Mobil) | 7% | 7% | | | |
| Dimethicone (and) Laureth-8 (and) Succinoglycan Mirasil ® DME-30 (Bluestar Silicones) | 4% | | | | |
| Dimethicone (and) Laureth-7 | | 4% | | | |
| Hydroxypropyl trimonium Hydrolyzed Wheat Protein | 0.5% | 0.5% | | | |
| Hydroxypropyl Guar Jaguar ® HP-8 (Rhodia) | | | 0.5% | | 0.5% |
| Propylene glycol | | | 2% | 2% | 2% |
| Cetearyl Octanoate | | | 2% | 2% | 2% |
| Cetyl Alcohol | | | 5% | 5% | 5% |
| Lauryldimonium Hydroxypropyl Hydrolyzed Keratin | | | 0.5 | 0.5 | 0.5 |
| Polyquaternium-2 Mirapol ® A-15 (Rhodia) | | | | 2% | 2% |
| Fragrance, preserving agents | qs | qs | qs | qs | qs |
| Water | qsp | qsp | qsp | qsp | qsp |

22) Hair Conditioners Compositions

| Constituents | Compositions | | | | |
|---|---|---|---|---|---|
|  | 134 | 135 | 136 | 137 | 138 |
| Glyceryl Stearate (and) PEG-100 Stearate | 0.3% | 0.3% | 0.3% | 0.3% | 0.3% |
| Polymer 1 | 0.2% | 0.2% | 0.2% | 0.2% | 0.2% |
| Polysorbate-60 Alkamuls T-80C (Rhodia) | 0.3% | | 0.3% | 0.3% | 0.3% |
| Silicone (Dimethicone) (and) laureth-7 or laureth-8 | 6% | 8% | 6% | 6% | 6% |
| Hydroxypropyl Guar Jaguar ® HP-8 (Rhodia) | | | | 0.2% | 0.2% |
| Stearyl Alcohol | 0.2% | 0.2% | 0.2% | 0.2% | 0.2% |
| Cetyl Alcohol | 0.3% | 0.3% | 0.3% | 0.3% | 0.3% |
| Quaternium-18 | 0.75% | 0.75% | | 0.75% | |
| Hydroxyethyl cellulose Natrosol ® 250-HHR HEC (Aqualon) | 0.5% | 0.5% | 0.5% | 0.5% | 0.5% |
| Fragrance, preserving agents | qs | qs | qs | qs | qs |
| Water | qsp | qsp | qsp | qsp | qsp |

23) Hair Conditioners Compositions

| Constituents | Compositions | | | | |
|---|---|---|---|---|---|
| | 139 | 140 | 141 | 142 | 143 |
| Cetyl Alcohol | 2.5% | 2.5% | 2.5% | 2.5% | 2.5% |
| Stearyl Alcohol | 1.75% | 1.75% | 1.75% | 1.75% | 1.75% |
| Glyceryl Stearate (and) PEG-100 Stearate | 1.2% | 1.2% | 1.2% | 1.2% | 1.2% |
| Stearamidopropyl Dimethylamine | 1% | 1% | 1% | 1% | 1% |
| Cetrimonium Chloride | 2.5% | 2% | 1.5% | 2% | 2.5% |
| Polymer 1 | 0.3% | 0.4% | 0.5% | 0.3% | 0.2% |
| Water & Dimethicone & Laureth-8 & Succinoglycan: Mirasil DME-30 KCG (Bluestar Silicones) | 1% | 1% | 1% | 1% | 2% |
| Preservative, citric acid, fragrance | qs | qs | qs | qs | qs |
| Water | qs 100% | qs 100% | qs 100% | qs 100% | qs 100% |

Same compositions could have been prepared with polymer 2, polymer 3 and polymer 4 also.

The invention claimed is:

1. A personal care composition comprising 0.2 wt. % to 0.9 wt. % of at least one guar derivative, the guar derivative comprising:
   i) a mean average molecular weight (Mw) from about 250,000 g/mol to about 600,000 g/mol; and
   ii) at least one hydroxypropyltrimethylammonium group, with a cationic degree of substitution $(DS_{cat})_{extraction}$, from about 0.20 to about 0.30,
wherein the weight percentage of the at least one guar derivative is based on the total weight of the personal care composition, and the personal care composition reduces wet combing work by at least 50% relative to compositions that do not contain the guar derivative.

2. The personal care composition according to claim 1, wherein the mean average molecular weight is from about 300,000 g/mol to about 600,000 g/mol.

3. The personal care composition according to claim 1, wherein the $(DS_{cat})_{extraction}$ is from about 0.20 to about 0.25.

4. The personal care composition according to claim 1, wherein the $(DS_{cat})_{extraction}$ is from about 0.25 to about 0.30.

5. The personal care composition according to claim 1 comprising 0.4 wt. % to 0.9 wt. % of the at least one guar derivative.

6. The personal care composition according to claim 1, wherein the personal care composition is a hair composition.

7. A shampoo composition comprising 0.2 wt. % to 0.9 wt. % of at least one guar derivative, the guar derivative comprising:
   i) a mean average molecular weight (Mw) from about 250,000 g/mol to about 600,000 g/mol; and
   ii) at least one hydroxypropyltrimethylammonium group, with a cationic degree of substitution $(DS_{cat})_{extraction}$, from about 0.20 to about 0.30,
wherein the weight percentage of the at least one guar derivative is based on the total weight of the shampoo composition, and the shampoo composition reduces wet combing work by at least 50% relative to compositions that do not contain the guar derivative.

8. The shampoo composition according to claim 7, further comprising silicone.

9. The shampoo composition according to claim 8, further comprising an antidandruff agent.

10. The shampoo composition according to claim 7 comprising 0.4 wt. % to 0.9 wt. % of the at least one guar derivative.

11. A method for
   i) providing conditioning effects to the hair; and/or
   ii) providing care to hair and/or scalp; and/or
   iii) providing a nice dry hair appearance;
   wherein said method comprises treating the hair in need thereof with the personal care composition of claim 1.

12. The method according to claim 11, wherein the hair is damaged hair.

13. A method for
   i) providing conditioning effects to the hair; and/or
   ii) providing care to hair and/or scalp; and/or
   iii) providing a nice dry hair appearance;
   wherein said method comprises treating the hair with the hair composition of claim 6.

14. The method according to claim 13, wherein the hair is damaged hair.

15. A method of treating hair, the method comprising treating the hair with a hair composition, wherein said hair composition comprises 0.2 wt. % to 0.9 wt. % of at least one guar derivative, the guar derivative comprising:
   i) a mean average molecular weight (Mw) from about 250,000 g/mol to about 600,000 g/mol; and
   ii) at least one hydroxypropyltrimethylammonium group, with a cationic degree of substitution, $(DS_{cat})_{extraction}$, from about 0.20 to about 0.30,
   wherein the weight percentage of the at least one guar derivative is based on the total weight of the hair composition, and the hair composition reduces wet combing work by at least 50% relative to compositions that do not contain the guar derivative.

16. The method of claim 15, wherein the hair composition comprises 0.4 wt. % to 0.9 wt. % of the at least one guar derivative.

* * * * *